(12) United States Patent
Smith et al.

(10) Patent No.: US 11,068,912 B2
(45) Date of Patent: Jul. 20, 2021

(54) MANAGEMENT SYSTEM AND METHODS OF MANAGING SALES DATA

(71) Applicant: One on One Sherpa, LLC, St. Louis, MO (US)

(72) Inventors: David A. Smith, University City, MO (US); Alexandra Fisher, Clayton, MO (US)

(73) Assignee: One on One Sherpa, LLC, St. Louis, MO (US)

( * ) Notice: Subject to any disclaimer, the term of this patent is extended or adjusted under 35 U.S.C. 154(b) by 1165 days.

(21) Appl. No.: 15/348,382

(22) Filed: Nov. 10, 2016

(65) Prior Publication Data

US 2017/0221079 A1    Aug. 3, 2017

Related U.S. Application Data

(60) Provisional application No. 62/253,322, filed on Nov. 10, 2015.

(51) Int. Cl.
| | | |
|---|---|---|
| *G06Q 10/06* | (2012.01) | |
| *G06Q 30/02* | (2012.01) | |
| *G06Q 50/16* | (2012.01) | |

(52) U.S. Cl.
CPC ......... *G06Q 30/0201* (2013.01); *G06Q 10/06* (2013.01); *G06Q 10/0637* (2013.01); *G06Q 10/06375* (2013.01); *G06Q 30/02* (2013.01); *G06Q 50/16* (2013.01)

(58) Field of Classification Search
CPC .............................. G06Q 10/06; G06Q 30/02
USPC ....................................................... 705/7.29
See application file for complete search history.

(56) References Cited

U.S. PATENT DOCUMENTS

| | | |
|---|---|---|
| 5,826,240 A | 10/1998 | Brockman et al. |
| 6,055,513 A | 4/2000 | Katz et al. |
| 6,125,356 A | 9/2000 | Brockman et al. |
| 6,349,290 B1 | 2/2002 | Horowitz et al. |
| 6,850,896 B1 | 2/2005 | Kelman et al. |
| 7,364,068 B1 | 4/2008 | Strubbe et al. |
| 7,370,004 B1 | 5/2008 | Patel et al. |
| 7,386,485 B1 | 6/2008 | Mussman et al. |
| 7,519,173 B2 | 4/2009 | Flores et al. |
| 7,711,599 B1 | 5/2010 | Libman |
| 7,922,493 B1 | 4/2011 | Gennaro et al. |
| 7,953,219 B2 | 5/2011 | Freedman et al. |
| 7,970,722 B1 | 6/2011 | Owen et al. |
| 8,103,530 B2 | 1/2012 | Quiring et al. |
| 8,103,531 B2 | 1/2012 | Wollan et al. |

(Continued)

FOREIGN PATENT DOCUMENTS

WO        199726610 A2    7/1997

*Primary Examiner* — Nga B Nguyen
(74) *Attorney, Agent, or Firm* — Stinson LLP

(57) ABSTRACT

A computer implemented method for managing sales information associated with a prospect. The method includes receiving data, at a processor, associated with the prospect; storing the received prospect data in a memory; analyzing, at the processor, the prospect data; generating, at the processor, a sales plan based at least on the analyzed data by generating at least one guideline; transmitting the at least one guideline to a sales member; receiving, at the processor, feedback data associated with the at least one guideline; and analyzing, at the processor, the received feedback data to update the sales plan based at least on the analyzed feedback data.

20 Claims, 34 Drawing Sheets

(56) References Cited

U.S. PATENT DOCUMENTS

| Patent/Publication | Date | Inventor | Classification |
|---|---|---|---|
| 8,204,884 B2 | 6/2012 | Freedman et al. | |
| 8,214,238 B1 * | 7/2012 | Fairfield | G06Q 10/063 705/7.11 |
| 8,311,863 B1 * | 11/2012 | Kemp | G06Q 10/0639 705/7.11 |
| 8,527,310 B1 | 9/2013 | Capetz et al. | |
| 8,533,025 B2 | 9/2013 | Davis et al. | |
| 8,660,872 B1 | 2/2014 | Sedota, Jr. et al. | |
| 8,868,448 B2 | 10/2014 | Freishtat et al. | |
| 2002/0073005 A1 | 6/2002 | Welnicki et al. | |
| 2002/0087385 A1 | 7/2002 | Vincent | |
| 2003/0069780 A1 | 4/2003 | Hailwood et al. | |
| 2003/0163365 A1 | 8/2003 | Farnes et al. | |
| 2003/0182175 A1 | 9/2003 | Buie et al. | |
| 2005/0044149 A1 | 2/2005 | Regardie et al. | |
| 2007/0038487 A1 | 2/2007 | McCarthy | |
| 2008/0140688 A1 * | 6/2008 | Clayton | G06Q 10/0637 |
| 2008/0183701 A1 | 7/2008 | Furman et al. | |
| 2008/0270148 A1 | 10/2008 | Morgen | |
| 2008/0312994 A1 * | 12/2008 | Clayton | G06Q 10/0637 705/7.35 |
| 2009/0248460 A1 | 10/2009 | Johnson | |
| 2009/0248479 A1 | 10/2009 | Johnson et al. | |
| 2009/0327037 A1 * | 12/2009 | Ng | G06Q 30/0244 705/14.43 |
| 2010/0010872 A1 | 1/2010 | Drummond et al. | |
| 2010/0223104 A1 * | 9/2010 | Patel | G06Q 30/02 705/7.35 |
| 2011/0258081 A1 | 10/2011 | Johnson et al. | |
| 2013/0006711 A1 * | 1/2013 | Biswas | G06Q 30/02 705/7.33 |
| 2013/0018963 A1 | 1/2013 | Brauff et al. | |
| 2013/0179790 A1 | 7/2013 | Nadiadi et al. | |
| 2014/0100876 A1 | 4/2014 | Savage et al. | |
| 2014/0279694 A1 * | 9/2014 | Gauger | G06Q 40/06 705/36 R |
| 2014/0323817 A1 | 10/2014 | El Kaliouby et al. | |
| 2015/0100528 A1 | 4/2015 | Danson et al. | |
| 2015/0149237 A1 | 5/2015 | Brock | |
| 2015/0254681 A1 | 9/2015 | Mahnken et al. | |

* cited by examiner

| PLANNING ADVANCES BASED ON PROSPECT'S STAGE OF READINESS |||| 
|---|---|---|---|
| Stage of Readiness | Prospect Behavior | Strategic Advance | Actions to help Prospect Advance |
| Stage 1 – Denial Stuck and hoping for magic | • Not fully aware or accepting of consequences of staying<br>• Defensive: deflects conversations about problems and difficulties in current living situation<br>• Initiative often comes from Spouse or Adult child | The Prospect is thinking about problems and difficulties in current residence. | • State Intentions – "help" not "sell" – align, build trust and validate feelings<br>• Acknowledge their control of the decision<br>• Explore expected outcomes of staying home without expressing judgment<br>• Evoke life stories and listen for themes and values |
| Stage 2 – Thinking About problems and difficulties: on the fence about "whether" | • Less defensive: willing to explore problems and difficulties in current residence<br>• Focus is "looking back" with some regret on how things used to be<br>• Ambivalent about "whether" to stay in current residence (Head knows, Heart isn't ready) | The Prospect has a willingness to acknowledge problems and desire to explore solutions | • Evoke stories about prior life changes that were successful.<br>• Promote self-evaluation of staying at home through use of reflections, amplifications and summaries<br>• Ask direct questions and probe their perceptions of each problem area and of likely future consequences |

FIG. 4A

| | | |
|---|---|---|
| Stage 3 – Planning Testing the waters but issue is "when" | • Acknowledges problems and difficulties of staying home are serious<br>• Ambivalent about "when" to address problems (not yet a priority)<br>• Looking to the future and open to discussing possible solutions | The Prospect is open to consider the benefits of making a change including a move to Senior Housing. | • Clarify Prospect goals. Don't assume that signs of readiness means they're ready to take action.<br>• Summarize the situation and elicit what they may want to do. Offer to resolve stated obstacles.<br>• Suggest options and encourage small steps. Get a commitment for something.<br>• Solicit collaboration with family/friends. |
| Stage 4 – Action Choosing "where" to move | • Issue is "where" to move<br>• Seeks information about your community: "Tell me more about…"<br>• Anxiety and possibility of a relapse increases when decisions become "real" | The Prospect makes a commitment – hopefully to move into your community | • Praise the decision to move – somewhere<br>• Provide information about you Product/Service package.<br>• Value match prospect needs to what your community offers.<br>• Ask for a commitment and offer to assist with perceived barriers |

FIG. 4B

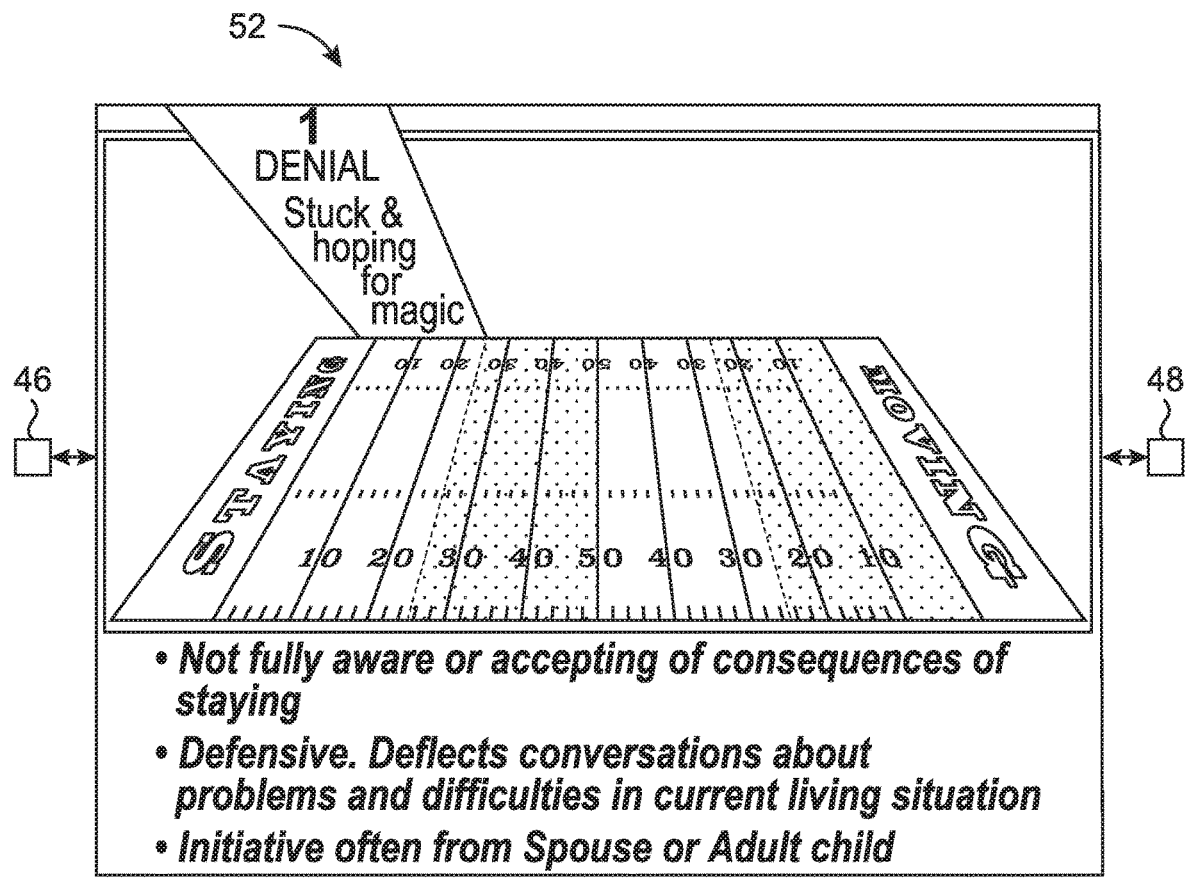

STAGE 1: DENIAL

Common defenses:
Making the least of it: Denial and minimization is a refusal to acknowledge unpleasant occurrences and pretend that disagreeable realities simply do not exist.

For example, read an excerpted interview with prospects Ed and Rozine.

*Counselor: How did you start the process of looking at assisted living communities?*

*Rozine: Our doctors told us we had no choice and would have to move to an assisted living community.*

*Ed: I don't really believe what he said. I'm going to see another doctor.*
*Counselor: Maybe you're hoping that someone says they were wrong the whole time?*

*Ed: That's right. I wish that they would look into it and see that it was all a mistake.*

FIG. 5A

Good Excuses:
Rationalization is the offer of a plausible explanation for staying, and intellectualization is the use of abstract analysis to rob events of personal significance.

*Counselor: Sounds like you want to delay mak- ing any decisions.*

*Ed: It's a tough thing to do. When we build this house we were planning to stay until they closed the casket. We have lived here for 37 ½ years now and accumulated a lot of things. You know, there're pictures and postcards on the wall. Do you keep those things or not? No way we can move before we get rid of all this stuff.*

Tuning Out:
Projection happens when a prospect points to someone else with the problem they are experiencing.

*Counselor: Who's making this decision today?*

*Ed: She is. She's the boss.*

*Counselor: Ed are you going to make it easier for Rozine?*

*Ed: Oh, yeah. I told her whatever you want to do. The decision to move is hard enough. It's easier to blame it on somebody else than to take it yourself.*

*Counselor: So Rozine, what would help you make a decision?*

*Rozine: I'm waiting to hear that Ed is ready to go and that he will follow through on the decision.*

Guidelines for helping prospects in denial
A strategic goal helps the prospect be- come more aware of their problems and difficulties so that they with begin to think about the possibility of moving.

1. State intentions to help not convince or persuade.
- Avoid taking on the role of the expert "who has all of the answers" and instead align, accept and validate.
- Don't substitute your views or assumptions about the "problems."

FIG. 5B

- Don't try to argue or push some- one into change until they are ready. Be patient.
- Don't give up or the prospect will loose confidence – stay en- gaged and be confident difficulties, implications and expected outcomes of staying at home.

*Counselor: We wanted to state our intentions, which is to just be here for the two of you – not just for today, but ongoing to be a resource, a support for you, regardless of whether you move anywhere or not. Our intention is to offer you our expertise and our resources if you need them. We understand that this is a decision that's very difficult for most people. We also understand that it's very much your decision, and you're in control.*

*Ed: So thank you very much.*

2. Align and build trusting relationships.
- Align – acknowledge their autonomy and control. Be accepting, attentive and curious.
- Establish an open, honest and non-judgmental rapport
- Empathetically engage and collaborate, as well as affirm and support.

3. Evoke discrepancy between the reality of continuing to live at home and what they really want for themselves.
- Ask open-ended questions to elicit life stories and other situation questions, and then listen for themes and values – what motivates the Prospect.
- Explore problems, difficulties, implications and expected outcomes of staying at home.
- Be aware of the adult child's or spousal am- bivalence. They struggle on the one hand with being a "good daughter" or being a "good wife" while on the other hand being objective and realistic about what is really happening. Try to pro- vide information and support to adult child.

FIG. 5C

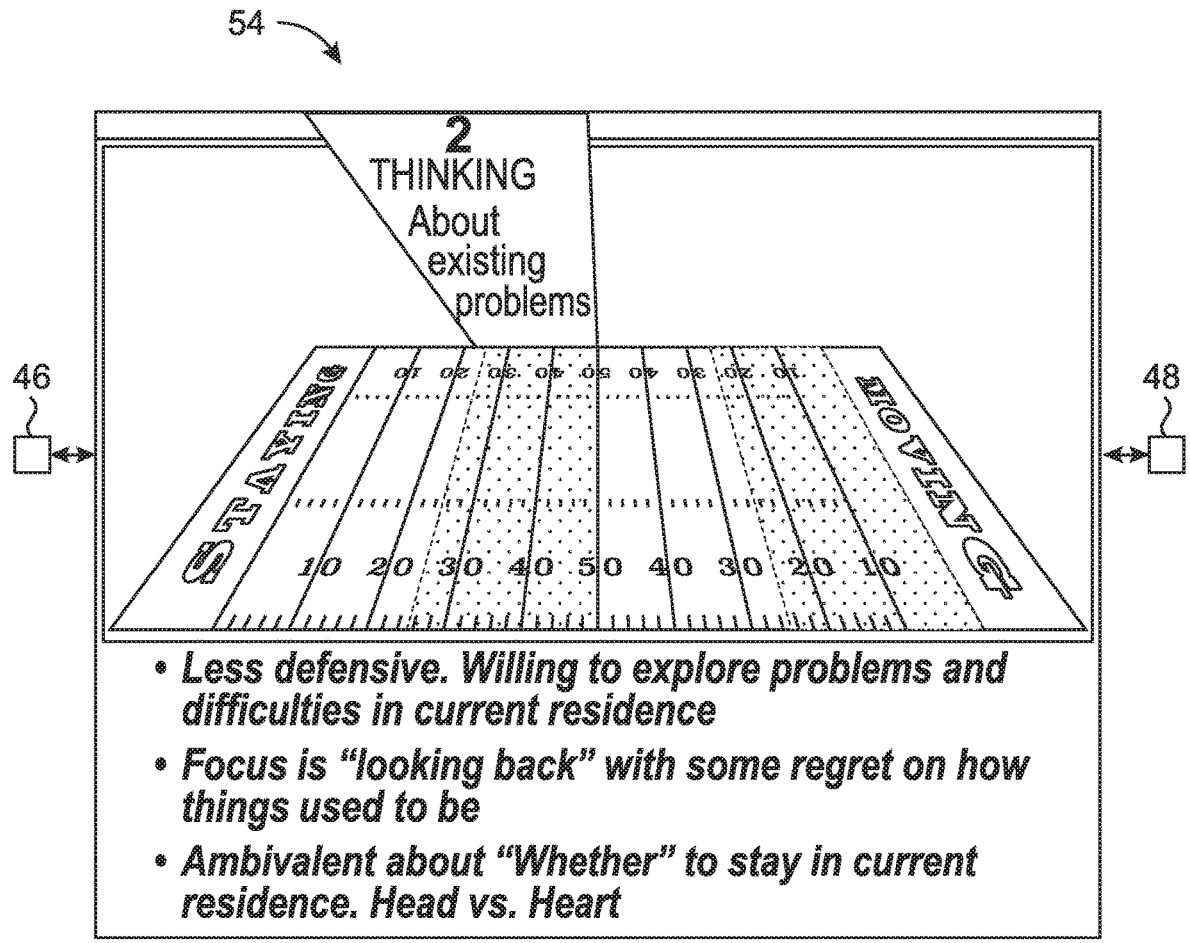

STAGE 2: THINKING

Guidelines to help Prospect Advance.
The strategic goal for Prospects in Stage 2 is to evoke "pro-change talk" where the prospect openly acknowledges problems and disadvantages in their current situation.

1. Intensify/Amplify Discrepancy - Ask more direct questions to clarify and elaborate on each of their problems and implications in the current situation.

- Ask for clarification: In what ways? How of- ten? When did you first notice? What was it like before . . . ?
   - Ask for a specific example. How did you feel about . . . ?
   - Ask for a detailed description of the last time this occurred.

FIG. 6A

- What concerns you the most about . . . ?
- Does that ever lead to . . . ?
- What effect does that have on . . . ?

2. Use motivational interviewing techniques including "reflections and summaries" to mirror and clarify responses.

- Form a reasonable guess as to meaning, and then give voice in the form of a statement and not a question—it's a statement of understanding intended to check rather than assume what you heard.

*Ed: When you get to this point, it's not what you thought. It's kind of like going and getting the cake and it's nothing but mush. But you've got to finally decide that you're not going to live for- ever. Someday you're going to have to close the casket.*

*Counselor: Wow, that's very interesting. What you are saying is that many people feel that a move to assisted living is closing the casket. Do you think that's true?*

- Reflection can move the thought forward rather than simply repeating like an echo.

*Ed: I see that things could get worse later than they are now. But we still haven't got rid of all of our stuff, and when you start downsizing, you lose your kitchen and actually you lose your house when you move into an assisted living community.*

*Counselor: You definitely would lose your house. There's no two ways about it. But if you wait for the house to be less important to you, you'll never move.*

*Ed: That's exactly right.*

3. Compare goals, values and themes drawn from life stories to the reality of their current living situation.

FIG. 6B

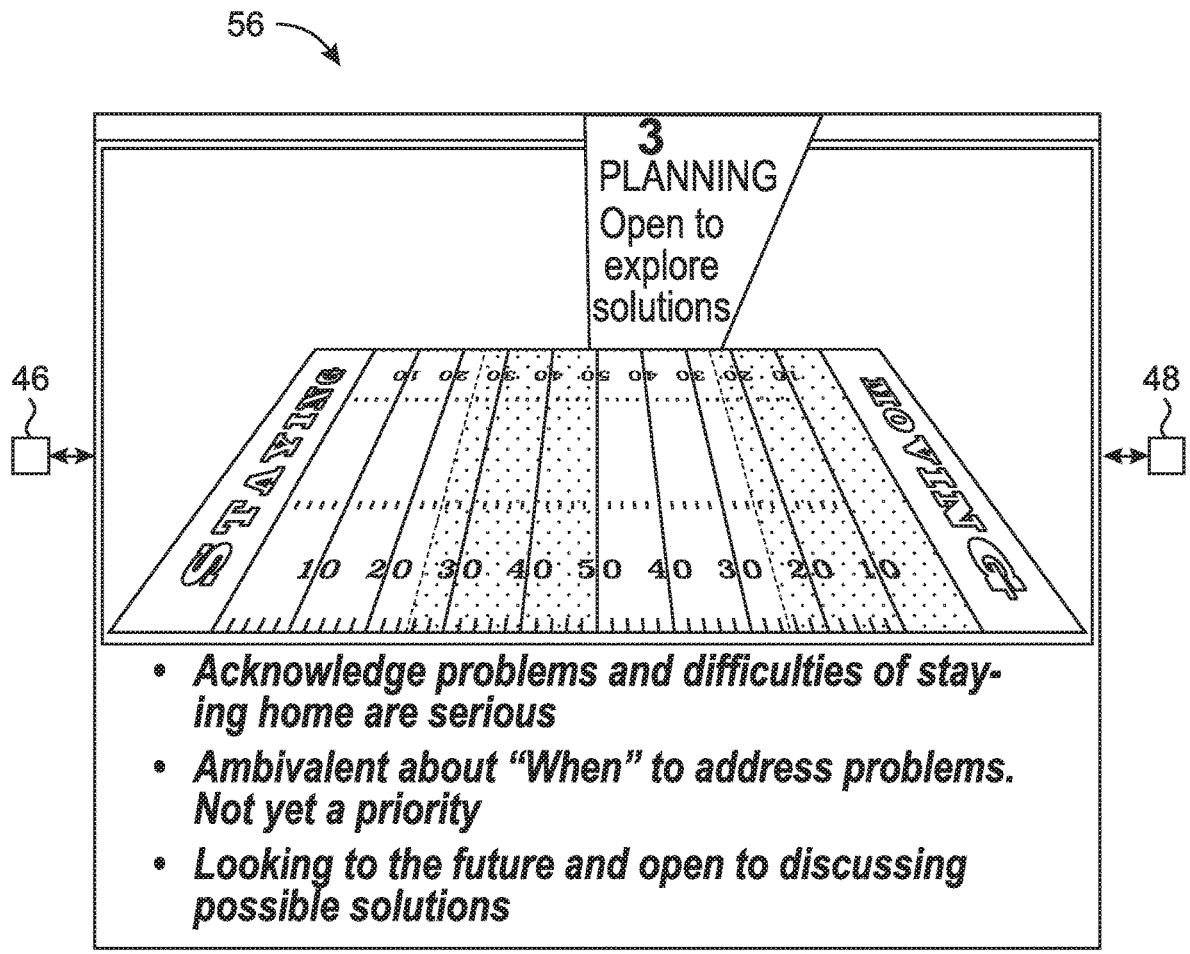

STAGE 3: PLANNING

Guidelines to help prospects advance from the planning stage.
The strategic goal is to generate inquiries about the benefits of making a change including, but not limited to, a move to senior housing and move towards getting some kind of commitment.

1. Avoid the temptation to assume that once the prospect is showing signs of readiness that they have made a decision to move. Most prospects take some tentative steps, still unsure of which way it is that they want to go. There usually is still quite a bit of ambivalence especially about "when" to move and a substantial risk of backsliding into an earlier stage of readiness.

FIG. 7A

2. A good first step is to summarize prospect's current situation as you have come to under- stand it, including:

- The prospect's perception of problems, difficulties and dissatisfactions of continuing to live in their current home
   - Summing up of both sides that make up the prospect's ambivalence including some acknowledgement of what remains positive or attractive about staying where they are
   - Review of any personal observations or evidence that may be relevant to change
   - Restatement of any statements from the prospect indicating that they may want, intend or plan to change 3. Try to elicit what the prospect may want to do to address perceived problems. Here are some sample questions:

- After reviewing all of this, what do you think should be the next step?
   - How do you see your options?
   - It sounds like things can't stay the way they are now. What do you think you might do?
   - Of the options you have considered, fixing up your home, bringing in some help, moving in with your daughter or moving to a senior community - which ones make the most sense to you?

4. Often at this stage the prospect will ask for advice. Provide relevant information about senior housing and your community and opportunities for them to visit and experience life there - but avoid the trap of trying to persuade.

- I don't know if this would work for you or not, but I can give you an idea of what some other people have done in your situation
   - This may or may not make sense to you, but it's one possibility
   - The best I can give you is my opinion. You are really the one that has to find what works best.

FIG. 7B

5. Help formulate a "change plan."

- Clarify what the prospect wants to achieve: "How would you like for things to be different?"
   - Discuss change options including a move to senior housing and to your community
   - Create a step-by-step action plan 6. Get a commitment for something. Consider smaller steps first:

- A return visit
   - Accepting your assistance with: a garage sale or developing a moving plan
   - Addressing any family concerns or resistance
   - Agreement to meet with existing residents or attend a, meal or, resident event.
   - Commitment for a trial stay 7. Get a commitment for something. Consider smaller steps first:

- A return visit
   - Accepting your assistance with: a garage sale or developing a moving plan
   - Addressing any family concerns or resistance
   - Agreement to meet with existing residents or attend a, meal or, resident event.
   - Commitment for a trial stay

FIG. 7C

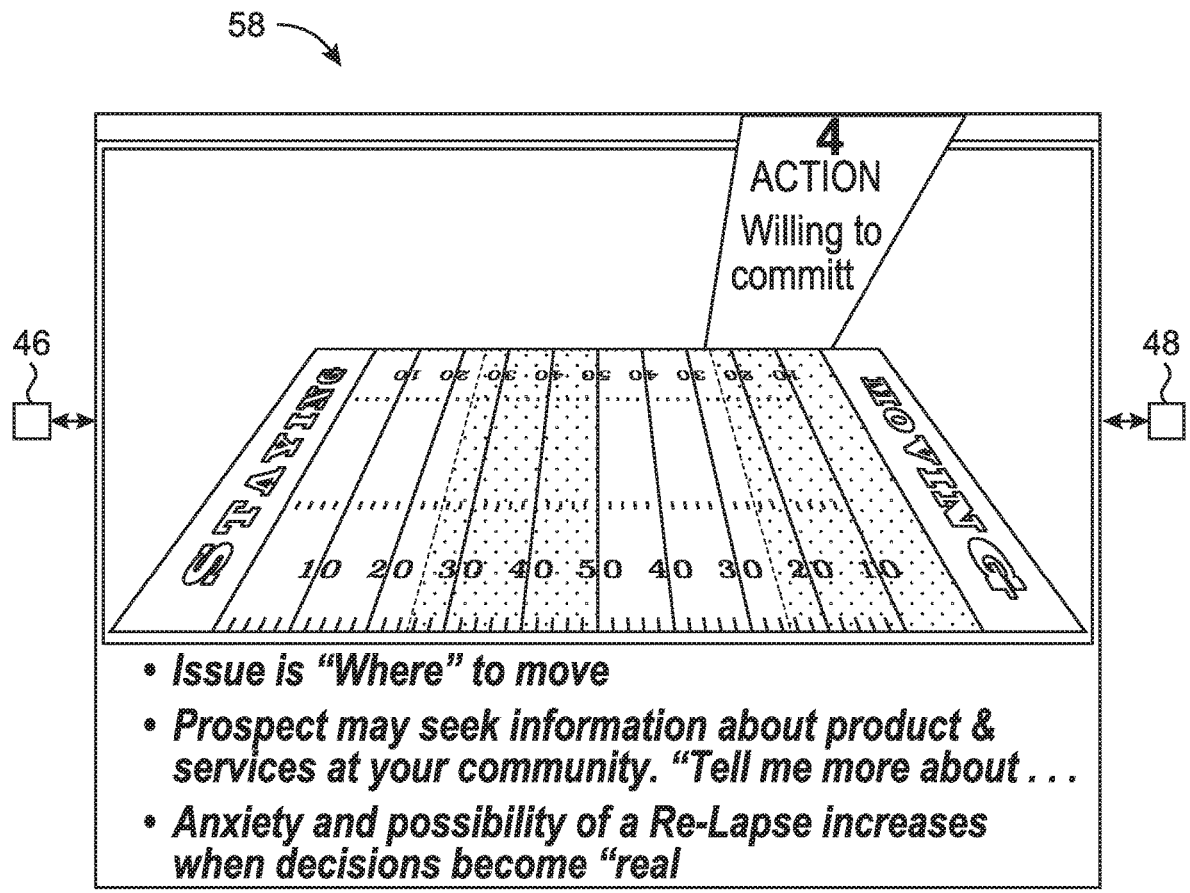

STAGE 4: ACTION

Guidelines to help prospects advance at action stage.

The strategic goal is to generate inquiries about the benefits of making a change including a move to senior housing and a move towards getting a commitment, deposit and move-in date.

- Engage in active discussion and education about senior housing and what's different and better about your community as compared to other options
- Match specific benefits in your community's programs and service offerings to prospect needs
- Describe leasing process and details and attempt to close on a unit with a move in date
- Solicit support and encouragement from prospect's family and support system

FIG. 8

Impact of Activities on Conversation Ratios by Top Sherpa Performers

A. Call In (15%)
B. Call Out (2%)
C. Email/Mail (2%)
D. Face to Face (39%)
E. Creative Follow-Up (23%)
F. Planning (19%)

Coaching Center

Search Coaching Center 🔍

Sherpa Coaching Center

Being A Sherpa
| Getting Started
| Prospect-Centered Selling
| Key Metrics (The Selling Zone)

Getting Prospects Ready
| Aging and Change
| Adult Children
| Stages of Change
| The sMART Grid Building Trust & Listening
| Be the Hero
| Discovery and Legacy
| Sample Questions
| Evoking Change Talk
| Home Visits

Welcome!

Your guide to better results

The Sherpa Coaching Center helps you learn and adapt Prospect-Centered Selling℠ to get the results you want. Have more effective conversations and make stronger connections with your prospects.

⬤sherpa | guiding change

Prospect-Cenetered Selling℠

[08:56] ▲ HD ✕

The Basics

Sample Questions

Sample Questions

See examples of questions that will guide you towards an Advance based on the *prospect's* Stage of Change.

Creative Follow-Up CFU

Creative Follow-Up (CFU)

Reach your prospects in thoughtful and creative ways in order to advcne the sale and make the most out of each interaction.

Getting Advances

Getting Advances

Find more ways to move your prospects along the *Stages of Change* toward an advance by asking for specific commitments or changes.

Stages of Change

Stages of Change

Replace a transactional approach to selling with one that measures progress under a continuum of changes from Denial to Action.

---

Planning & Advances
| The Case Study
| Team Planning
| Creative Follow-Up (CFU)
| Getting Advances More Good Stuff
| SMARTMarketing
| Glossary
| Useful Resources Tutorials

Contact

If you have a question, or if you are unable to find what you're looking for, please contact Sherpa at:

Phone:
314-432-1234

Email:
support@sherpacrm.com

◀Home  Admin Tools ▼  Onboarding Tools ▼  Kelly Stein... ▶

● sherpa        Analytics  Coaching

Coaching Center

Search Coaching Center 🔍

Sherpa Coaching Center

Being A Sherpa
Getting Started
  Prospect-Centered Selling
  Key Metrics (The Selling Zone)

Getting Prospects Ready
  Aging and Change
  Adult Children
  Stages of Change
  The sMART Grid Building Trust & Listening
  Be the Hero
  Discovery and Legacy
  Sample Questions Getting Started

Let's take the first step of your journey together.

Sherpa creators David Smith and Alex Fisher have worked in the senior living industry as developers, owners, sales leaders and trainers with a combined 30+ years of experience.

To them, selling senior housing is about helping people. But while incredible benefits should sell themselves, this is hardly ever the case.

Prospects who want or need an improved quality of life have many emotional barriers to overcome and will likely say "I'm not ready!"

Using their experiences in the "selling trenches," David and Alex have developed Prospect-Centered SellingSM that combines the best of relationship-based and transactional sales. Their methods have consistently produced higher visit-to-close conversion ratios and better sales results compared to conventional sales techniques.

The concepts and techniques that drive their trainings and sales campaigns are at the core of Sherpa, a web-based CRM designed to inspire, enable and track better senior housing sales. Sherpa is both a lead tracking and sales coaching tool that will help you make better connections, get the most out of your interactions and help your prospects take steps toward a positive change.

Identify how "ready" your prospect is and find opportunities to connect with them using Prospect-Centered SellingSM

- Develop an accurate picture of your prospect's readiness for change
- Effectively use case study templates, action plans and creative follow-up materials
- Focus on activities and behaviors that make your team effective; maximize your time in the Selling Zone
- Track and measure advances, the small steps that lead to a prospect deciding to move to your community

| Evoking Change Talk
| Home Visits

Planning & Advances
| The Case Study
| Team Planning
| Creative Follow-Up (CFU)
| Getting Advances More Good Stuff
| SMARTMarketing
| Glossary
| Useful Resources Tutorials

Contact

If you have a question, or if you are unable to find what you're looking for, please contact Sherpa at:

Phone:
314-432-1234

Email:
support@sherpacrm.com

Prospect Profile

John Doe

PROSPECT | SALES SUMMARY | INFLUENCES

Age: 92
1234 Green Lane
St. louis, MO 65432
Ph: 123-456-7890
Em: jdoe@mail.com

EDIT PROFILE

VIEW PHOTO/
ATTACHMENTS (4) ▲

+≗ ADD PROSPECT    Search ▼

Stage: Thinking ▼    Status: Active ▼ Top Ten

| 4 | 1 | 1 | 4 | 1 | 2 |
|---|---|---|---|---|---|
| ADV | T | HV | V2V | CFU | PCS |

12:15 Time in Selling Zone

Sales Journal    +

Case Study

Strategy
Open Actions
01/24/17 Appointment    03/22/2017 5:00PM    Elena B., Henry B. ×

Biography

Life Story
Lorem ipsum dolor sit amet, consectetur adip

| Search Journal Entries 🔍 SEARCH | iscing elit, sed do eiusmod tempor incididunt ut labore et dolore magna aliqua. Ut enim ad minim veniam, quis nostrud exercitation ullamco laboris nisi ut aliquip ex ea commodo consequat. |
|---|---|
| Displaying: 1-9 of 9 Journal Entries | |
| 03/22/2017 5:00PM (Matt L.)    📅 ✏️<br>Bulk Email Out 00:00<br>Bulk Action: test - test<br>Strategy: None | Duis aute irure dolor in reprehenderit in voluptate velit esse cillum dolore eu fugiat nulla pariatur. Excepteur sint occaecat cupidatat non proident, sunt in culpa qui officia deserunt mollit anim id est laborum. |
| | Sed ut perspiciatis unde omnis iste natus error sit voluptatem accusantium doloremque laudantium, totam rem aperiam, eaque ipsa quae ab illo inventore veritatis et quasi architecto. |
| | Legacy/Themes Values ✏️ |
| 01/21/2017 12:55PM (Henry B.)    📅 ✏️<br>Continuation                Call Out 00:15<br>John was happy to hear my voice. I talked to John more about his story, and if he's interested in coming in for a face-to-face discussion. He agreed and will come in this Wednesday.<br>Strategy: Continue to talk to John about his thoughts on a studio. And if he's interested in a tour of a sample studio.<br>Appointment (Elena B., Henry B.)<br>01/24/2017 | Excepteur sint occaecat cupidatat non proident, sunt in culpa qui officia deserunt mollit. |
| | Typical Day ✏️ |
| | Et harum quidem rerum facilis est et expedita distinctio. Nam libero tempore, cum soluta. |

FIG. 15B

Health

At vero eos et accusamus et iusto odio dignissimos ducimus qui blanditiis praesentium.

Financial

Et harum quidem rerum facilis est et expedita distinctio. Nam libero tempore, cum soluta. Nobis est eligendi optio cunque nihil impedit quo minus id quod.
Maxime placeat facere possimus, omnis voluptas assumenda est, omnis dolor repellendus. Temporibus autem quibusdam.

Adult Children/Influences

Motivators

Problems inCurrent Living Situation

Sed ut perspiciatis unde omnis iste natus error sit.

---

01/02/2017 2:00PM  (Henry B.)      Call Out, PCS  00:35

Continuation

Called John and asked how he was doing. Talked for some time about his financial options. He seems more than qualified for a studio in AL. He seemed excited to hear this.

Strategy: Reach out to John in a few weeks to see how he's coming along, and what his thoughts are on a studio. And if he's interested in a tour of a sample... Read Full Entry     (Henry B.)

✓ Call Out
   01/21/2017

---

11/26/2016 2:00PM                  Event  00:30

Continuation

John stopped by for a little while and seemed to enjoy the Spring Fling. I caught up quickly with John as he was leaving, and he said he wanted some time to think about it. He said to call back in... Read Full Entry

Strategy: Call out in a few months

✓ Call Out
   01/02/2017

FIG. 15C

| 10/29/2016 2:30PM  Elena B.  🗓 ✏ |
|---|
| Advance                              Call Out 00:45 |
| Talked to John for some time about his hesitations; he really is chatty once he feels comfortable with you. I asked John if he wanted to attend the Spring Fling in early May, to which he said yes! |
| Strategy: Check on John throughout the Spring Fling and make sure he's comfortable. |
| ✓ Event Attendance |
| 11/26/2016 |

| 10/11/2016 12:30PM  Elena B., Brie R., Henry B  🗓 ✏ |
|---|
| Continuation    PCS, Creative Follow Up   05:15 |
| Developed a strategy for John, and sent CFU of a model airplane. I did some digging and sent him the same type of airplane he flew in the war. |
| Strategy: See if he enjoyed the model airplane, and ask if he's interested in attending an event. |
| (Elena B.) |

| 10/01/2016 4:00PM  Elena B.  🗓 ✏ |
|---|
| ✓ Call Out |
| 10/29/2016 |

Objections ✏

Concerns About Moving Now

Iscing elit, sed do eiusmod tempor incididunt ut labore et dolore magna aliqua.

Ut enim ad minim veniam, quis nostrud exercitation ullamco laboris nisi ut aliquip ex ea commodo consequat.

Preferences ✏

Desired Features & Benefits

Questions (0)

[ Add New Question                    + ]

FIG. 15D

Continuation      Home Visit 01:30

Learned more about John's life story (refer to Life Story section) and troubles getting up the stairs. Tom lightly pushed John to admit that it was hard to him to walk up the stairs, and after a...Read Full Entry

Strategy: Conduct a planning session for John, send CFU of a model airplane.

✓ Planning (PCS)     (Elena B., Brie R., Henry B)
    10/09/2016

✓ Creative Follow Up     (Elena B.)
    10/09/2016

---

09/18/2016 9:00AM   (Elena B., Henry B.)     Tour 03:10

Advance

Tom came in with John to get a tour of the place. John was a bit shy, but after asking him a few questions, he really seemed to blossom. He told us about stories from the war, his medal for....Read Full Entry

Strategy: Conduct a home visit with John and learn more about his life story.

✓ Call Out     (Elena B.)
    10/01/2016

---

08/23/2016 9:00AM   (Elena B.)     Call In 00:15

Advance

Tom called in looking for information for his father, John. He asked if he could bring in John next month for a tour; he's currently easing him into the idea of moving.

FIG. 15E

Sherpa Technical Specification Document  ◆sherpa| guiding change

| Hosting Locations and Server Security | |
|---|---|
| Hosting Provider | Sherpa is a cloud hosted application on Amazon AWS. |
| Server Configuration | Sherpa utilize an Ubuntu server in a Virtual Private Cloud (VPC) hosted on dedicated hardware. |
| Server Location | Our servers are hosted in Amazon's Eastern region in multiple data centers throughout Virginia. The physical hardware is a minimum of 50 kilometers apart. In addition we have a reserved server in Amazon's West region in their Oregon data center. |
| Database Access | Direct access to the Sherpa databases are strictly limited to Sherpa Employees who have access to both encrypted PEM keys and ssh keys. |
| Network | |
| Protocols | Standard https on port 443 |
| Recommended Bandwidth | Bandwidth ranges of 1.5 Mbps (T1) and greater with latencies no greater than 100ms. |
| Wireless Compatibility | The application is available wirelessly through an internet connected device running a current browser. |
| Wireless Channel Requirements | None |
| Interface Dependencies | None |
| Additional Specialized Requirements | None |
| VPN Connection Required | No |
| Server | |
| User Authentication | Users are authenticated by entering a user name (email address) and password that are housed internal to the application. The user data is encrypted and passwords are salted to ensure that no user, including Sherpa support, has direct access to a users plain text passwoerd |
| Active Directory Requirements | None |

FIG. 16A

| | |
|---|---|
| ADFS Requirements | None |
| Internal Domain Requirements | None |
| External Domain | None |
| Does the application require remote Desktop Support? | None |
| Operating Systems | Windows, Mac, Android |
| Installation Instructions | There are no installation instructions for our application. The user enters our URL into their browser and accesses the site. |
| Drive Mapping(s) Required | None |
| Special procedures required to upgrade system | None |
| Mobile operating system | There is no separate mobile version. The application will run on any mobile device that has a current browser installed. |
| Support | |
| Support paradigm to include SLAs | Phone and email support 7 days (6AM-12AM). 95% calls handled with first contact; usage support 24 hours. |
| Support methodology | Our support is more extensive than other Software CRM's in the industry. |
| Local support requirements | System supports company and community level administrators with additional usage capabilities. Usability and system support is entirely through our support team. |
| IS staff training requirements | IT support is typically required. |
| System manager training | No client side management is required; client administration training during initial user system training. |
| What kind of end user training is provided? | On-Site Day long system and sales training. Additional new user trainings are offered bi-weekly. Also provide comprehensive review and update post 30 days, 90 days, and six month to assure proper utilization, on-demand webinars as needed. |

FIG. 16B

| | |
|---|---|
| Electronic manuals available | Upon request |
| Application update requirements | No client-side tools required. Updates are handled by Sherpa with no installation or upgrades required by the client. |
| Support services located outside the continental United States | None |
| Report generation and development | End user will typically run a report within Sherpa that has already been made available system wide. Specific reports not otherwise included can be created by support team. |
| Application | |
| Application tenancy architecture | This is a single tenancy application architecture. |
| Source code accessibility | Sherpa has access to the source code. The client will not as this is not needed. |
| Application software upgrade availability | The Sherpa Software development team manages upgrades to the software. We are not on a set time table for upgrades. We do notify the client prior to releasing upgrades as well as offer tutorials to the client in the event the upgrade impacts the user |
| Application upgrade testing | Sherpa is responsible for all testing prior to an application upgrade being released. |
| Data conversion process/tools | Yes. We work around the clients data structure and what data extraction methods are available to them. The Sherpa Team then transforms that data into the correct Sherpa Templates and will import the data directly into the application. A final review of the data once in Sherpa is performed with the client during the initial Training. |
| Load balancing and log monitoring | Sherpa monitors these logs. |
| Database maintenance | Any table or database maintenance will be performed by Sherpa. |
| Security | |
| Access logging | We currently have the capability to do so. We maintain authorization logs as well. |

FIG. 16C

| | |
|---|---|
| Log retention | This can be configured per client request. |
| Log review | Per client request |
| Password requirements | A password is required for a user to access Sherpa. The password is set by the user and Sherpa employees do not have access to the plain text password at any time. |
| Password encryption | Passwords are encrytped and never stored in plain text. |
| Sherpa support accounts | The support accounts are minimal and managed internally by Sherpa. |
| Application roles | We employ a role based authentication system. |
| Application backup retention | Yes |
| How long are backups retained? | 7 days |
| Backup encryption | Backups are encrypted and stored on AWS on a different server |
| ISSS (Desktop) | |
| Minimum Workstation Requirements (Hardware, Software, Prerequisites | An internet connected device running a modern web browser |
| Display Limitations or Requirements | The application is scaled to 1024 but is viewable in smaller resolutions with scrolling. |
| Special Printer/Printing Requirements | None |
| Open Shares on Servers or Desktops Requirements | None |

FIG. 16D

COMMUNITY COMPARISON REPORT

The following Report reflects a Year-to-Date Data comparison of two communities that utilize Sherpa for ongoing management of sales information.

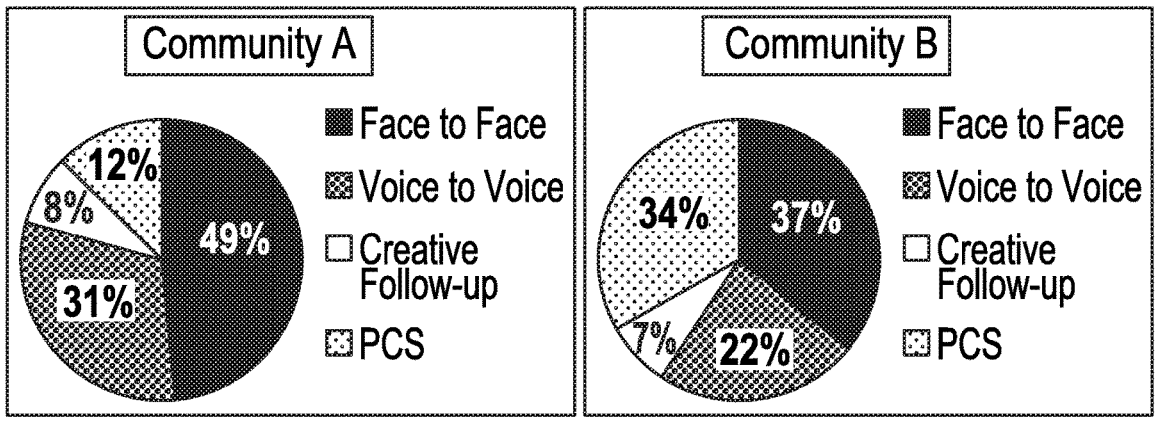

The charts above illustrate the distribution of sales activity types for each community.

| Data Category | Community A | Community B |
|---|---|---|
| Current Occupancy Rate | 94% | 99% |
| Leads Worked | 800 | 600 |
| TSZ per Lead Worked | 2.6 hours | 4.3 hours |
| Total Move Ins | 35 | 47 |

Conclusion: *Sherpa data reveals increased time in the selling zone per lead results in a higher number of Move ins with a smaller lead base.*

*Per Move in Averages*

| *Activity type/Total* | *Community A* | *Community B* |
|---|---|---|
| *Face to Face* | *5* | *5* |
| *Voice to Voice* | *28* | *20* |
| *Prospect Case Study* | *1* | *10* |
| *Creative follow Up* | *1* | *5* |
| *Leads per vacant unit* | *115* | *45* |
| *Advances* | *7* | *9* |
| *Days in Lead Base* | *747* | *411* |

FIG. 17

MANAGEMENT SYSTEM AND METHODS OF MANAGING SALES DATA

CROSS-REFERENCE TO RELATED APPLICATION

This non-provisional application claims priority to U.S. Provisional Patent Application Ser. No. 62/253,322, filed on Nov. 10, 2015, which is hereby incorporated by reference in its entirety.

BACKGROUND

The embodiments described herein relate to a data management system, and more particularly, to data management systems and methods for receiving, managing, analyzing, and/or transmitting information relating to sales techniques.

Typical lead management and customer relations management systems classify prospects and create sales pipeline milestones based on the level of urgency perceived by the sales person. Typically, these are simplified into three categories: "Hot"; "Warm"; and "Cold". Sales time and resources are then allocated and prioritized so that the most urgent leads get the most time and attention. In the case of senior housing, only a small percentage (for example, roughly 10%) of qualified prospects actually "buys". Conventionally, these prospects are driven by a serious health or other crisis. Based on the value of the offering to these higher acuity prospects, the costs to provide needed care; and/or the total expected revenue based on anticipated length of stay, those that are "ready" to buy are lesser valuable customers. On the other hand most (90% or more) qualified prospects are not "ready" to move and instead choose to stay where they are rather than moving to any of the communities in their respective markets.

Some sales techniques for senior housing use "transactional sales". Transactional sales focus on matching customer needs with supplier offerings (product or service). Traditional sales techniques may include simply asking questions to uncover customer needs; making offers; handling objections; and, trying to close sales deals. Typical sales activities may turn into routines in order to drive the selling cycle to a minimum number of points of contact with the individual prospects. Transactional sales models may view success from the perspective of how the transaction is progressing toward a move-in decision.

For senior housing sales, typical new inquiries can relate to an older adult that is struggling with physical and/or mental problems, difficulties and dissatisfactions in their current living situation that negatively affect their quality of life. These issues generally involve chronic health issues that limit normal functioning or unfulfilled needs associated with: personal safety; lack of socialization; poor nutrition; personal care oversight; medication management; family dynamics; self-expression; and, home maintenance. Given the benefits offered by the many and varied senior housing options, senior housing should sell itself to older adults. However, strong emotional resistance may result in over 90% of qualified prospects being "not ready" to change their living situation, even if a change would result in a significantly better quality of life.

For senior housing sales, four milestones are typically tracked and measured: inquiry, initial tour, deposit, and move-in. The milestones are set up to measure and report the number of sales activities (primary call-outs, tours, and deposits) based on the assumption that the level of sales activity directly correlates with and is useful predictor of the prospect's progress through the sales pipeline.

Current sales techniques and milestones for senior housing sales are transaction centered. There is a need, however, in the senior housing industry for sales techniques that are prospect centered. Moreover, there is a need in the senior housing industry for sales techniques that provide specific and action orientated guidelines. Still further, there is a need in the senior housing industry for a computer implemented sales method and data management system that produces higher visit to close conversion rates.

DRAWINGS

These and other features, aspects, and advantages will become better understood when the following detailed description is read with reference to the accompanying drawings in which like characters represent like parts throughout the drawings, wherein:

FIGS. 4A-4B depicts is an exemplary table and a schematic illustrating sales strategies and actions of a prospect's stage of readiness for the data management system of FIG. 1;

FIGS. 5A-5C illustrate an exemplary outline, an exemplary scenario, and a schematic for a sales stage for the data management system of FIG. 1;

FIGS. 6A-6B illustrate another exemplary outline, an exemplary scenario, and a schematic for another sales stage for the data management system of FIG. 1;

FIGS. 7A-7C illustrate another exemplary outline, an exemplary scenario, and a schematic for another sales stage for the data management system of FIG. 1;

FIG. 8 illustrates another exemplary outline, an exemplary scenario, and a schematic for another sales stage for the data management system of FIG. 1;

Figure 12A:
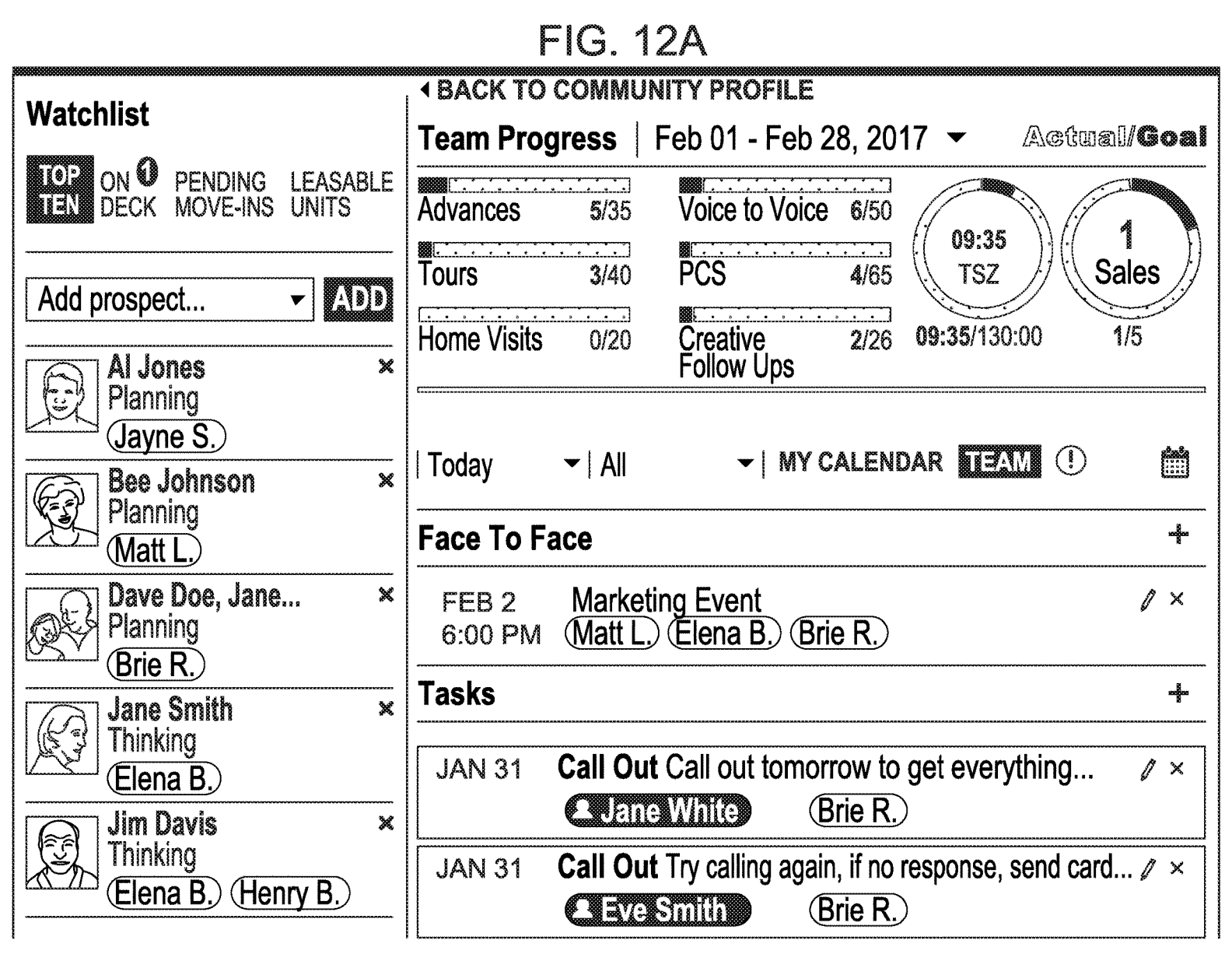
Figure 12B:
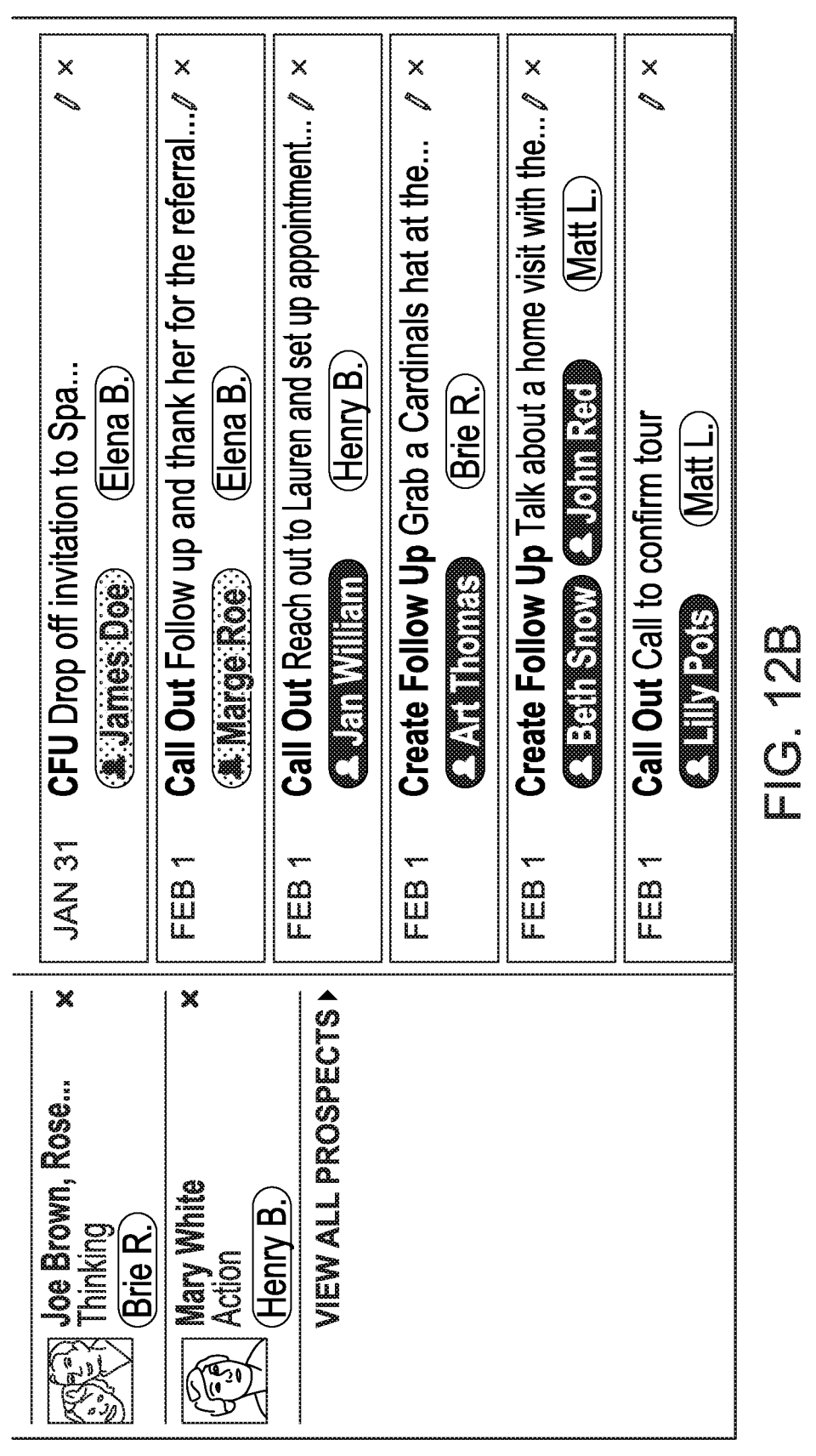

FIGS. 12A-12B depict exemplary screenshots of a web page of the exemplary data management system;

FIGS. 13A-13B depict exemplary screenshots of a web page for a guide for prospect-centered selling of the exemplary data management system;

FIGS. 14A-14B depict exemplary screenshots of a web page of the exemplary data management system;

Figure 1:
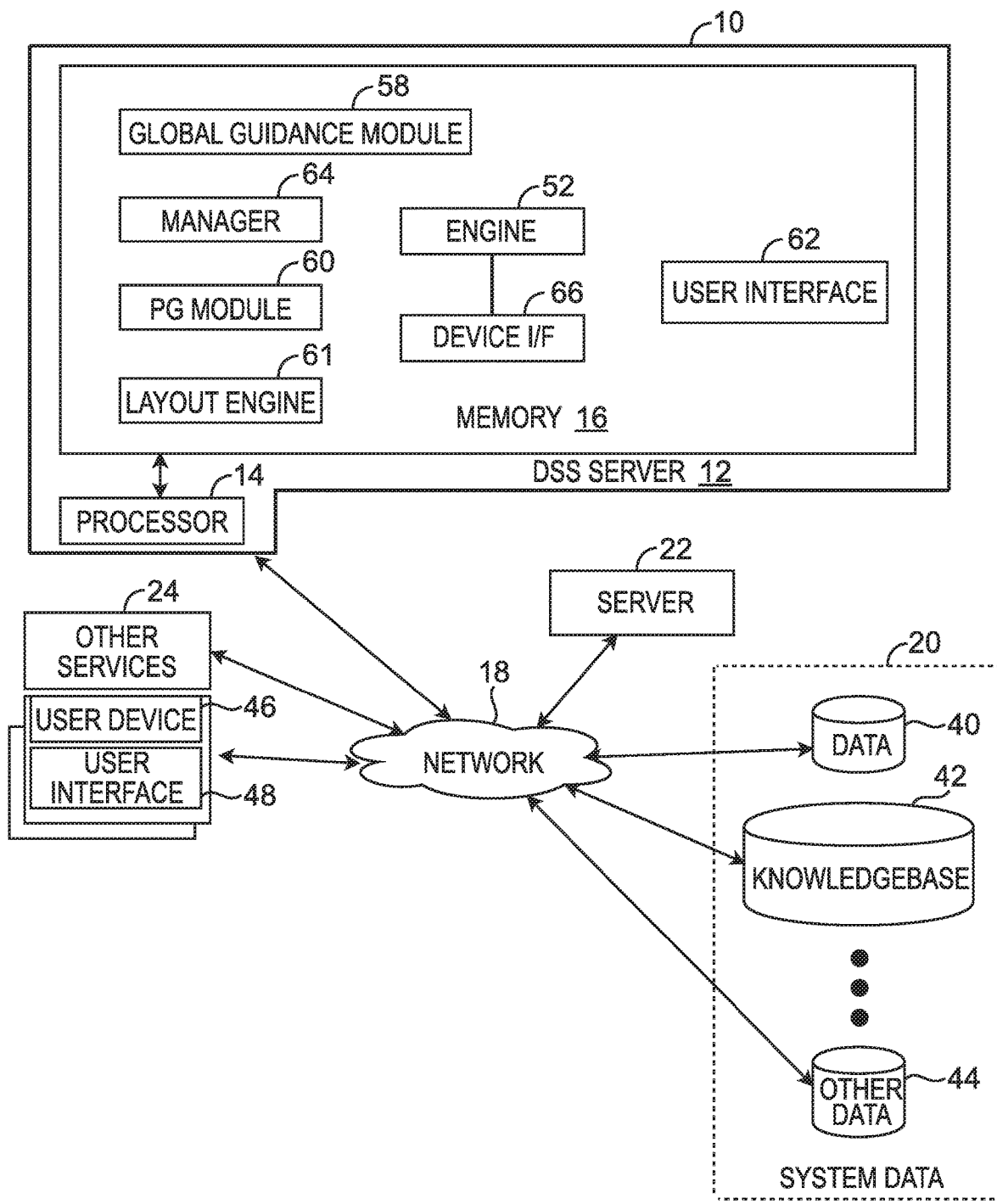
FIG. 1 is a schematic view of an exemplary data management system for a prospect centered sales method.

15A-15E are other exemplary screenshots of web pages of the exemplary data management system;

FIGS. 16A-16D illustrate exemplary technical specifications of the exemplary data management system; and FIG. 17 is an exemplary comparison report of two communities that utilize the prospect-centered selling of the exemplary data management system.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

The embodiments described herein relate to systems and methods of a data management/sales system, and more particularly, to data management/sales systems and methods for producing higher "visit-to-close" conversion rates. The incremental gains from this computer implemented approach correlate stronger with higher-functioning independent and assisted living prospects, the ones who are not forced to move due to an immediate crisis. However, the prospect is not limited to a certain category of seniors. The prospect-centered program includes spending more time in the "selling zone", building trust by asking more and better questions, personalized creative follow-ups, and planning advances along a series of distinct "Stages of Change." The prospect-centered program of the exemplary embodiments is prospect/customer centered rather than product centered. The approach is to align with the prospect in a non-judgmental way, build trust, discovering who they are, and assess the extent to which they are ready to change. It should be understood that the embodiment described herein includes a variety of sale prospects, and further understood that the descriptions and figures that utilize "senior living" sales are exemplary only. The exemplary system is configured to work for any type of sales prospect such as, but not limited to, real estate, insurance, financials, and other products or services.

Rather than trying to convince or persuade, the prospect-centered program of the exemplary embodiments relates to the prospect in a manner that is collaborative, evocative, and reflective. In the early stages of readiness, prospect-centered sales counselors invest time building relationships, learning the prospect's life story, and planning purposeful initiatives designed to help them confront their emotional resistance relative to a change in housing. During the sales process, each prospect's behavior and statements are associated with at least one of four stages of readiness: denial, thinking, planning, and action.

The system is configured for a relationship-based selling method that consistently produces higher sales conversion ratios, especially with higher functioning prospects, that are not already facing an immediate crisis. The system is configured to address underlying emotional resistance with techniques designed to raise awareness and promote self-persuasion before offering the option of senior housing as a solution. The relation-based selling of the system is characterized by spending more time building relationships with prospects before they reach a need-driven crisis. This selling style is supported with: deliberate and ongoing planning for each prospect face-to-face or voice-to-voice interaction; extensive journaling of prospect statements and conversational patterns; and, creative, personalized follow-up initiatives. The system facilitates sales counselors to inspire and motivate reluctant prospects to advance towards a decision to make lifestyle changes by providing specific, action-oriented guidelines.

In the exemplary embodiment, the descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage to refer to these signals as bits, values, elements, symbols, characters, terms, numbers or the like.

It should be understood, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processor", "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The embodiments also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks. CD-ROMs, and magnetic-optical disks, read-only memories (ROMs), random access memories (RAMs), EPROMs. EEPROMs, magnetic or optical cards, or any type of media suitable for storing electronic instructions, each coupled to a computer system bus.

The embodiments can take the form of an entirely hardware embodiment, an entirely software embodiment or an embodiment containing both hardware and software elements. In a preferred embodiment, the exemplary embodiment is implemented in software, which includes but is not limited to firmware, resident software, microcode, etc. Furthermore, the exemplary embodiment can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk.

Current examples of optical disks include compact disk-read only memory (CD-ROM), compact disk-read/write (CD-RAW) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks, modems, cable modem and Ethernet cards are just a few of the currently available types of network adapters.

The software, algorithm and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is described with reference to a particular programming language. It will be appreciated that a variety of programming languages may be used to implement the teachings of the invention as described herein. Moreover, the present invention may include security protocols and programs such as, but not limited to. Amazon web services (www.amazon.com/security).

Figure 2:
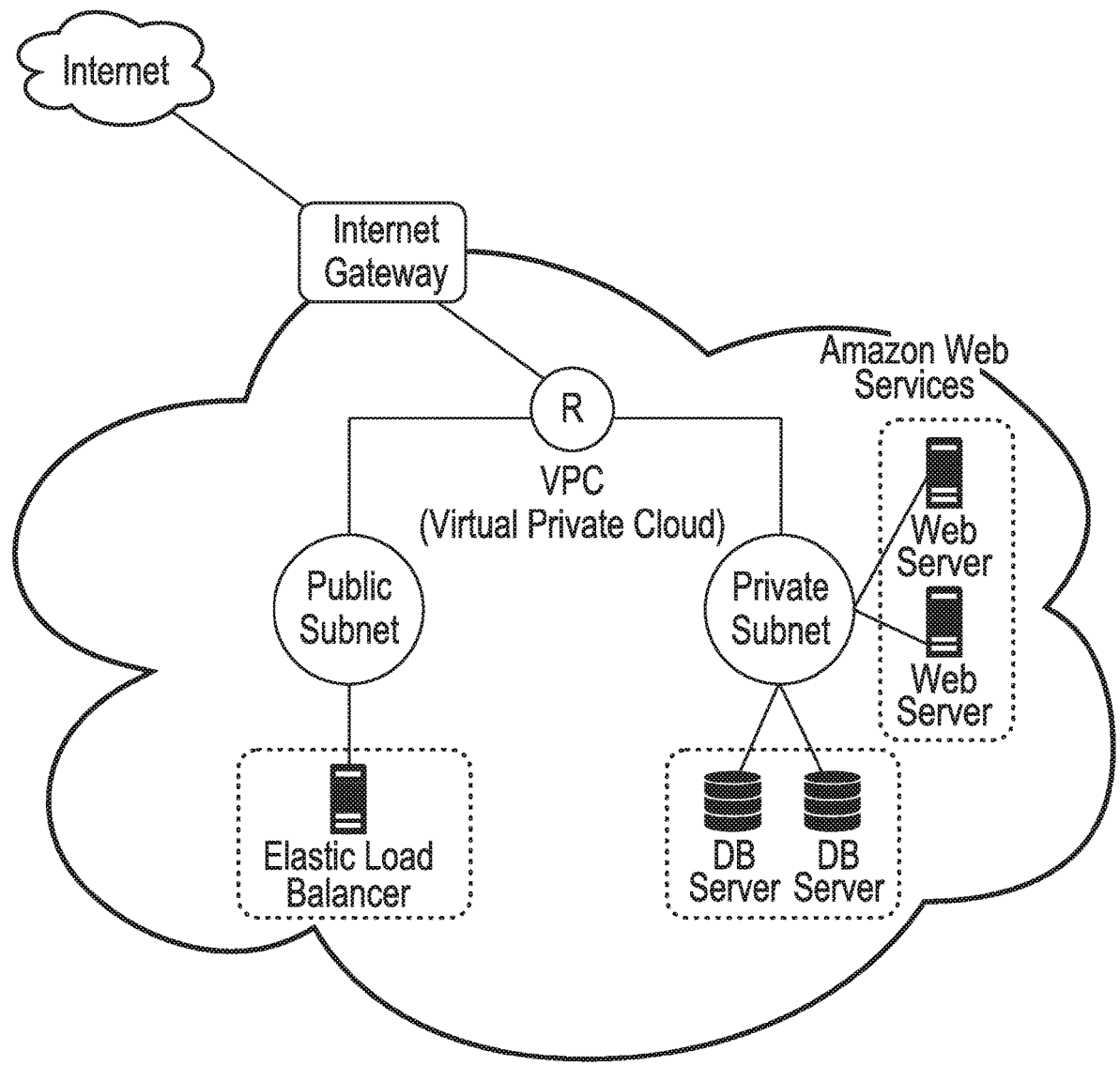
FIG. 2 is a schematic view of an exemplary architectural diagram of the data management system of FIG. 1.
Figure 3:
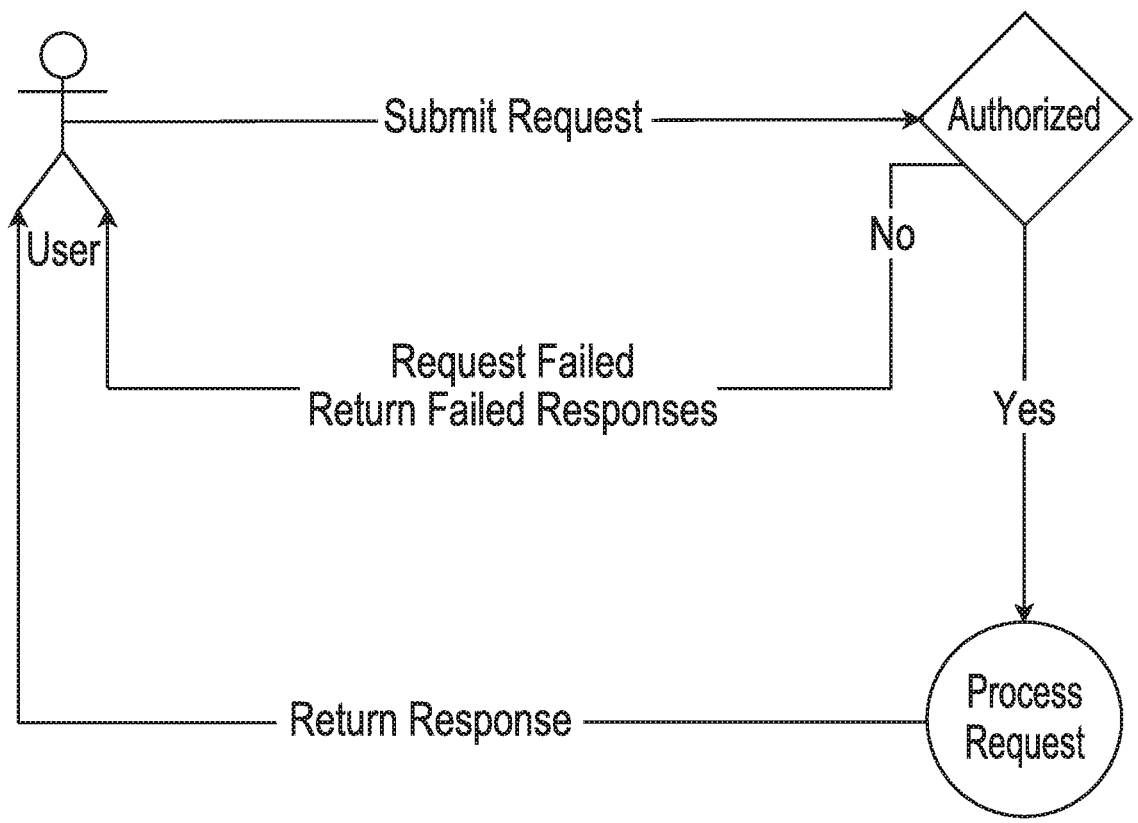
FIG. 3 is schematic view of an exemplary flow diagram relating to processing requests for the data management system of FIG. 1.

FIG. 1 depicts a data management system 10 for a prospect centered selling method. FIG. 2 is a schematic view of an architectural diagram of the data management system 10. FIG. 3 is a schematic view of an exemplary flow diagram relating to processing requests of the data management system 10. In an embodiment, the user can be, but not limited to, a sales person, a sales team, a sales associate, a sales manager, a sales representative, and a sales counselor. Moreover, in an embodiment, the prospect can be a person (or, for example, a person associated with the prospect such as a legal guardian, family member, client or agent) looking to buy a service and/or a product such as, for example, senior housing living. The management system 10 includes a server 12. The server 12 can include one or more processors 14 and memory 16. The memory 16 can store data and machine readable instructions that can be executed by the processor 14. For example, the memory 16 can comprise physical memory, such as can reside on the processor 14 (e.g., processor memory), random access memory or other physical storage media (e.g., CD-ROM, DVD, flash drive, hard disc drive, etc.) or a combination of different memory devices that can store the machine readable instructions. The memory 16 further can be implemented within a single machine, as depicted in FIG. 1, or it can be distributed across multiple machines. The data utilized for implementing the systems and methods described herein can also be stored in the memory 16 or in some other arrangement of one or more memory structures that are accessible for use by the management system 10.

The server 12 can be connected to a network 18 such as to provide for communication between the management server and various services, devices and data stores that can collectively form the system 10. The network 18 can be a local area network, a wide area network, or a combination of different various network topologies, which may include physical transmission media (e.g., electrically conductive, optical fiber media or the like) and/or wireless communications media, that can be utilized for communicating information. The network or at least a portion of the methods and functions implemented thereby can operate in a secure manner (e.g., behind a firewall separated from public networks) and/or utilize encryption for data communications. As a further example, the server 12 can be implemented as a computing cloud in which the functions and methods and data can be accessible as a service via the network 18.

The server 12 can employ the network 18 to access system data 20, an encounter server 22, as well as one or more other services generally indicated at 24. These other services 24 can correspond to various other servers that can store and provide information pertinent to a given sales associate, prospect and/or client. Such other services 24 may also execute methods and functions that can be utilized by the server 12, such as via corresponding application interfaces. The particulars of such other services 24 can vary according to the particular purpose of the management system 10.

In addition to prospect data, client data and sales data that may be stored in a database 40, the server 12 can also access a knowledge base 42 or one or more other data sources, indicated at 44. The knowledge base 42 can be utilized to access a variety of information and matching algorithms that may be utilized by users of the system 10. Such information contained in the knowledge base 42 or the other data sources 44 may be accessed via a search engine. The server 12 can make such information available to its users via dynamic or configurable links. As an example, the server 12 can present information to a user via one or more web (e.g., html) pages that contain dynamic links (e.g., hypertext links) to predefined resource locations (e.g., uniform resource locations (URLs)) at which pertinent information corresponding to the system data 20 can be provided. As disclosed herein, the server 12 can be programmed to automatically select the information according to the real-time conditions of the sales associate and/or prospect/client, preferences of the user, guidance expressions and other information related to an associate input; prospect/client request, and/or matching decisions relative to the sales associate and prospect/client. The server 12 can provide an encounter GUI (e.g., a page) that is populated with such selected information and/or links to such information.

Authorized users can also employ one or more corresponding user device 46 to access information generated by the server 12. There can be any number of user devices 46 that can access the information from the server 12. A given user device 46 can include a user interface 48 that allows the user to access the functions and methods implemented by the server 12 as well as to retrieve related content information. The user interface 48, for example, can include a web browser (or a thin client application) that can be provided dynamic links for accessing the functions and methods corresponding to the server 12. It is to be appreciated that such user device 46 can be a computer, a work station, as well as a mobile device (e.g., a smart phone, laptop or tablet computer) that can run a corresponding application programmed to access the functions and methods associated with the server 12. The user device 46 can be located in a corresponding local area as well as can be implemented as a remote device that can access the information produced by the server 12, such as by accessing corresponding pages via a web browser or other application.

The server 12 can include an engine 52 programmed to evaluate information and data pertinent to an evolving prospect enrollment and/or prospect selection process. The engine 52 can receive the data from various inputs, as well as from data available from other sources such as the system data 20, the encounter server 22 and other services 24. The engine 52 can be programmed to analyze such information based on one or more expressions and compute decision support data that can be employed to populate a visualization space that is presented to one or more users. The engine 52 can also be programmed to search the system data 20 or other sources for pertinent associate enrollment and/or client selection process. For example, the system 10 can automatically generate matching criteria by populating the visualization space with relevant information and/or links to information stored in the knowledge base 42 or in the other data 44. Data acquired by the server 12 can be stored in the memory 16 or another database, such as may be part of the system data 20.

The system 10 can also include an engine 61 that is programmed to control populating the layout of a visualization space. The layout can include a static layout, a dynamic layout or a combination of static and dynamic layouts. A static layout, for example, can be configured to provide guidance and support data for each of one or more predefined positions in a visualization space. For example, a user can select a set of locations (e.g., different associates) and the layout engine 61 can populate the visualization space with a GUI element to provide guidance information for each selected location. In this example, the layout engine 61 can populate the visualization space with the GUI element for each location statically (e.g., regardless of the results of any expressions). The engine 61 can also dynamically populate the visualization space based on one or more expressions that are assigned to visualization space. For example, a user can assign an expression to a place holder in the visualization space and only populate the space with a corresponding GUI element depending on the results of the assigned expression. Thus, if the expression criteria is met, the engine 61 can dynamically add a GUI element and if (or when) the criteria is not met any longer, the GUI element can be removed from the visualization space. In this way, the system 10 can employ one or more selected expressions to dynamically control populating a layout based on encounter data.

A user can employ a user interface 62 of the server 12 that can access corresponding tools, such as may be part of a manager 64. The manager 64 can correspond to functions and methods that can be utilized to program or various aspects of the system 10, such as disclosed herein. The accessibility of various functions and methods that can be accessed by a given user can depend upon an individual's authorization or role within the system. For example, there can be any range of roles that can be established within the system 10, which may be based upon existing authentication systems for an enterprise or network in which the system 10 is being implemented. For instance, a supervisor or other individual with a sufficient level of authorization can set the parameters for controlling the global guidance module 58.

A system administrator further may be able to create and configure interfaces, such as including one or more device interfaces 66, to control communication and retrieval of data from various resources in the system 10. The device interface 66 thus can create a communications channel via the network for retrieving relevant data. The retrieved data can include raw data, processed data or a combination of raw and process data that can be presented in the form of content to a given user. Additionally, an individual user may also employ the user interface 62 to access personal preferences via the manager 64, such as to establish parameters that control the personal guidance module 60 for such user, set up user devices 46 and other personal settings.

In the exemplary embodiment, the data management system 10 is a web-based SaaS (software as a service) application designed to inspire, enable, analyze and track better senior housing sales. In addition to counting, tracking and reporting common sales tasks and activities, the data management system 10 is configured for intuitive workflows that support relevant sales behaviors and help sales counselors identify ways to advance the sale beyond "I'm not ready" to guide each user to achieve better sales performance. The data management system 10 is configured to facilitate more efficient, economical, and faster operations by the processor 14.

Moreover, the data management system 10 is configured to help the sales team to: identify new opportunities for connecting with prospects and supporting best sales practices through a coaching center; capture an accurate picture of a prospect's readiness for change; and, strategize using prospect case study templates, next step action plans and creative follow-up activities for the sales person. Additionally, the data management system 10 is configured to focus and maximize time in the selling zone by the sales person which can include: face-to-face, voice-to-voice, personalized planning and creative follow-up.

The system 10 is configured to create use, update, and/or report a comprehensive daily agenda to the sales person to help prioritize and focus sales efforts such as: appointments for the day, creative follow up from yesterday or any previous time period, top 10 case studies and execution of prospect action plans. Additionally, the system is configured to receive, track and/or measure advances while quantifying the sales team's activities, current occupancy, and prospect sales status.

The data management system 10 is configured for data from organic, visual and easy to access prospect profiles. The profiles enable sales teams to create a lifestyle and decision-making overview of each prospect. The data management system 10 also facilitates uploading photographs, documents and other materials relative to the prospect. For sales managers, the system has a separate dashboard with real time access to key metrics relative to individual sales personnel and/or sales team. Relevant data can be compiled, reported and graphed by the data management system 10 based on a variety of sorting factors, including: length of time since initial inquiry, pending follow up plans, new inquiries and most recent advances.

The data management system 10 is configured to facilitate sales managers to measure and track the factors relevant to determining a sales pipeline and sales effectiveness. The data management system 10 records and sorts key sales activities captured by existing customer relation management systems, presenting the data in unique graphs and charts for easy analysis. A user-friendly management dashboard of the data management system 10 provides an overview of key indicators such as: a view a productivity and a team statistics overview; easily access saved reports; a view a sales effectiveness summary; a check occupancy and lead summary statistic; highest and lowest performing communities for percentage occupied; and, analyze at least, for example only, the last 10 move-ins to facilitates replicating success. Additionally, the data management system 10 is configured to create customized prospect and mailing lists through the system's search feature by using filters such as, but not limited to, lead status, stage of change, specific lead or referral source information, and an apartment/housing preference.

In an embodiment, the processor 14 of the data management system 10 is configured to program instructions for a plurality of steps for the computer-implemented sales method. More particularly, the processor 14 is configured to program a first step of scheduling initial conference calls with the sales team and key stakeholders from the sales/customer team. The processor 14 generates discussions focused on challenges with existing customer relation management systems, how existing data is used, and the criteria that will be used by the sales person to evaluate a successful transition. The processor 14 includes executing instructions for another step of creating a specific plan that outlines the major milestones and key activities involved based on the customer's success criteria. The plan is configured by the processor 14 to facilitate preparing the organization and the sales team for a smooth onboarding for the prospect.

The processor 14 is configured to execute instructions for another step of defining success criteria, wherein the data migration is planned in partnership with the sales person. The sales team walks through the final data elements for approval before the final import. Moreover, the processor 14 is configured to execute instructions for another step of creating and scheduling delivery within 24-48 hours post data migration to prevent any gap in sales operations. The processor 14 executes instructions for another step of creating and providing functional and technical support via quick response, self-service, and regularly scheduled webinars based on the complexity of the issue and the prospect's communication preference.

FIGS. 4A-4B shows a table and a schematic illustrating sales strategies and actions of the prospect's stage of readiness 50 of the data management system 10 between a sales person 46 and a prospect 48. The processor 14 of the data management system 10 is configured to provide guidelines for distinct screening filters for determining where the prospect 48 is on the change continuum relative to the stage of readiness 50. The processor 14 is configured to identify behaviors and statements that characterize each stage and instruct the sales person 46 to build trusting relationships, engage in purposeful questioning, active listening, as well as extensive journaling, planning and follow-up. At any time during the sales process, the processor 14 is configured to associate each prospect's behavior and statements with one of four stages of the stage of readiness 50. No one stage is considered to be more important than another; and, linear progression through all of the stages is possible. Depending on what triggers the initial inquiry, the prospect 48 can start out at any one of the four stages. In general, the more crisis driven and higher acuity the prospect 48 is in, the more ready the prospect 48 is likely to be. Alternatively, the stage of readiness 50 can include less than four stages or more than four stages.

FIGS. 5A-5C illustrates an outline, scenario, and schematic for a sales stage of the stage of readiness 50 relative to a "denial" stage 52 of the prospect 48. In the prospect's denial stage, the prospect's behavior includes parameters such as not being fully aware or accepting consequences of staying in the current living environment. Additionally, the prospect's behavior includes being defensive or deflecting conversation about the problems and difficulties in the current living environment. In the exemplary embodiment, the processor 14 is configured to generate outlines and guidelines that relate to the prospect's "denial" stage 52. The processor 14 receives, from the sales person 46, data associated with the prospect 48. In the exemplary embodiment, the prospect data can include information such as, but not limited to: health information, financial information, family information, and activity/hobby information. The received prospect data is stored in the memory; and, the processor 14 analyzes the prospect data. The processor 14 generates a sales plan based at least on the analyzed data by generating at least one guideline. The sales plan is configured to generate a user strategy correlating that the prospect 48 is thinking about problems and difficulties in the current living environment.

In the embodiment, the processor 14 is configured to generate guidelines for the sales person 46 for helping prospects 48 in denial. More particularly, the processor 14 is configured to generate the guidelines of stating intentions by the sales person 46 for helping the prospect 48 and not convincing or persuading a prospect's decision. The generated intentions include for example only: avoid taking the role of the expert who has all the answers and instead align, accept, and validate the prospect's feelings: don't substitute views or assumptions about the problem; and, don't try to argue to push the prospect 48 into change until the prospect 48 is ready. The processor 14 is further configured to generate additional guidelines of aligning and building trust and relationships between the sales person 46 and the prospect 48. The generated guidelines include, for example only, acknowledging the prospect's autonomy and control; establish and open, honest and non-judgmental rapport; and, engage and elaborate as well as a form of support. The processor 14 is configured to generate additional guidelines of evoking discrepancy between the reality of continuing to live at home and the prospect's wishes. Moreover, the processor 14 is configured to generate guidelines of evoking life stories from the prospect 48 and to develop themes and values of the prospect 48. Still further, the processor 14 is configured to generate guidelines for the user to address adult child ambivalence and to educate in response thereto.

FIGS. 6A and 6B illustrates an outline, scenario, and schematic for another sales stage of the stage of readiness 50 relating to a "thinking" stage 54 of the prospect 48. In the prospect's thinking stage, the prospect's behavior includes parameters such as being less defensive and willing to explore problems and difficulties in the current living environment. Additionally, the prospect's behavior includes a focus of looking back with some regret on how things used to be previously in the prospect's life. The prospect 48 becomes ambivalent whether to stay in the current living environment.

Since the prospect 48 has a willingness to acknowledge problems and desires to explore solutions, the processor 14 is configured to generate outlines and guidelines that relate to a prospect's "thinking" stage 54 for the sales method. In the embodiment, the processor 14 is configured to generate guidelines for the sales person 46 to facilitate prospects 48 to think about a living situation. More particularly, the program is configured to generate the guidelines for the sales person 46 relating to clarifying the prospect's current living situation. Additionally, the processor 14 is configured to provide the sales person 46 motivational interviewing techniques including reflections and summaries to mirror and clarify responses. The generated guideline includes forming a reasonable guess as to meaning, and then gives voice in the form of a statement and not a question—rather a statement of understanding intended to check rather than assume what the sales person 46 heard.

In the exemplary embodiment, the processor 14 is configured to generate a comparison of goals, values and themes drawn from life stories to the reality of the prospect's current living situation. The processor 14 is configured to generate guidelines for the sales person 46 to evoke stories about prior life changes of the prospect 48 that were successful. Moreover, the processor 14 is configured to generate sales person guidelines for the sales person 46 to promote self-evaluation by the prospect 48 of staying home through tools such as reflections, amplifications and life summaries. Still further, the processor 14 is configured to generate direct questions for the sales person 46 to probe the prospect's perceptions of each problem area and possible future consequences.

FIGS. 7A-7C illustrate an outline, scenario, and schematic for another sales stage of the stage of readiness 50 relating to a "planning" stage 56 of the prospect 48. In the planning stage, the prospect's behavior includes parameters such as acknowledging problems and difficulties of staying in the current living environment can be serious. Additionally, the prospect's behavior includes looking to the future and open to discussing possible solutions. In the exemplary embodiment, the processor 14 is configured to generate outlines and guidelines for the sales person 46 that relate to the prospect's behavior stage for the sales plan. The sales plan generated by the processor 14 is configured to generate a strategic advance for the sales person 46 correlating that the prospect 48 is open to consider the benefits of making a change including a move to senior housing. In the exemplary embodiment, the processor 14 is configured to generate guidelines for the sales person 46 to create inquiries about the benefit of making a living change including, but not limited to, a move to senior housing and a move towards getting a commitment. The processor 14 is configured to generate guidelines for the sales person 46 for summarizing the prospect's current situation. These guidelines include: the prospect's perception of problems, difficulties and dissatisfactions of continuing to live in the current home; summing up of both sides that make up the prospect's ambivalence including some acknowledgement of what remains positive or attractive about staying where they are; a review of any personal observations or evidence that may be relevant to change; and, a restatement of any statements from the prospect 48 indicating that they may want, intend or plan to change.

Moreover, the processor 14 is configured to generate questions for the sales person 46 relating to what the prospect 48 may want to do to address perceived problems. The generated questions include: after reviewing all of this, what do you think should be the next step?; how do you see your options?; it sounds like things can't stay the way they are now. What do you think you might do?; of the options you have considered—fixing up your home, bringing in some help, moving in with your daughter or moving to a senior community—which ones make the most sense to you.

In the embodiment, the processor 14 is configured to provide relevant information about senior housing and committing to opportunities for the prospect 48 to a visit. Additionally, the processor 14 is configured to generate solicitations to collaborate with the prospect's family or friends. Moreover, the processor 14 is configured to generate a change plan which clarifies what the prospect 48 wants to achieve and to create a step by step plan. Still further, the processor 14 is configured to generate a commitment follow up for the sales person 46 which include steps such as: a return visit; assistance with a garage sale or a moving plan; address any family concerns or resistance; agreement to meet with the existing residents, attend a meal or a resident event; and, commitment for a trial stay.

FIG. 8 illustrates another outline, scenario, schematic for another sales stage relating to an "action" stage 58 of the prospect 48. In the action stage 58, the prospect's behavior includes parameters such as questions on where to move and to seek information about senior housing. In this action stage, there is anxiety and possibility of relapse by the prospect 48 to increase when a decision becomes real. In the exemplary embodiment, the processor 14 is configured to generate outlines and guidelines relating to an "action" stage for the sales method. For example, the processor 14 transmits the at least one guideline to the sales person 46. The processor 14 is configured to generate guidelines for the sales person 46 such as to praise the prospect's decision to move to senior housing. Moreover, the processor 14 is configured to provide information about the senior housing to the prospect 48. Still further, the processor 14 is configured to generate guidelines for the sales person 46 such as providing information about senior housing and value match the prospect's needs with the senior housing. The guidelines, generated by the processor 14, include instructions to solicit support and encouragement from the prospect's family and/or support system. Additionally, the guidelines, generated by the processor 14, include describing the leasing process and details and attempt to close on a unit with a move in date. The sales member acts on the guidelines and received feedback data from the interaction with the prospect 48. The processor 14 receives the feedback data from the sales person 46 associated with the at least one guideline; and analyzes the received feedback data. The sales plan is updated by the processor 14 based at least on the analyzed feedback data.

Figure 9:
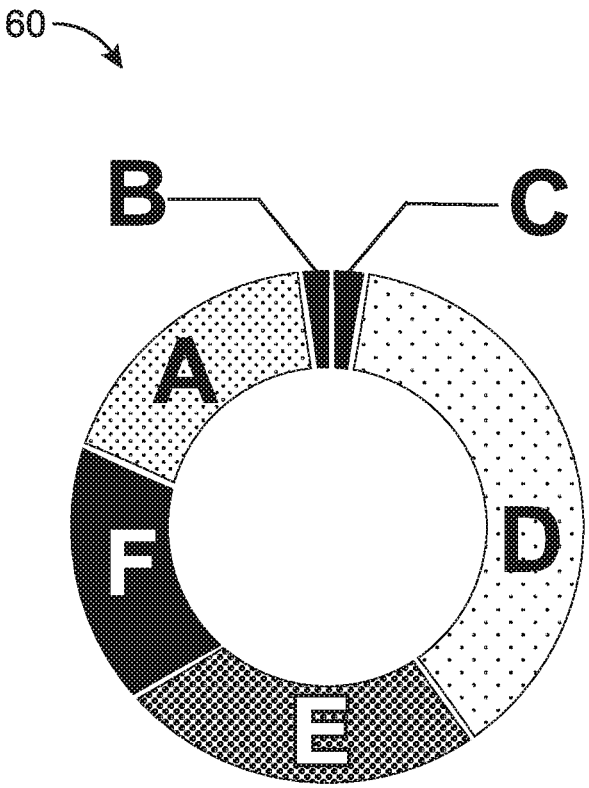
FIG. 9 is a chart representing a research study conducted utilizing the data management system and the impact of activities on conversion ration by top sales users of the data management system.
Figure 10:
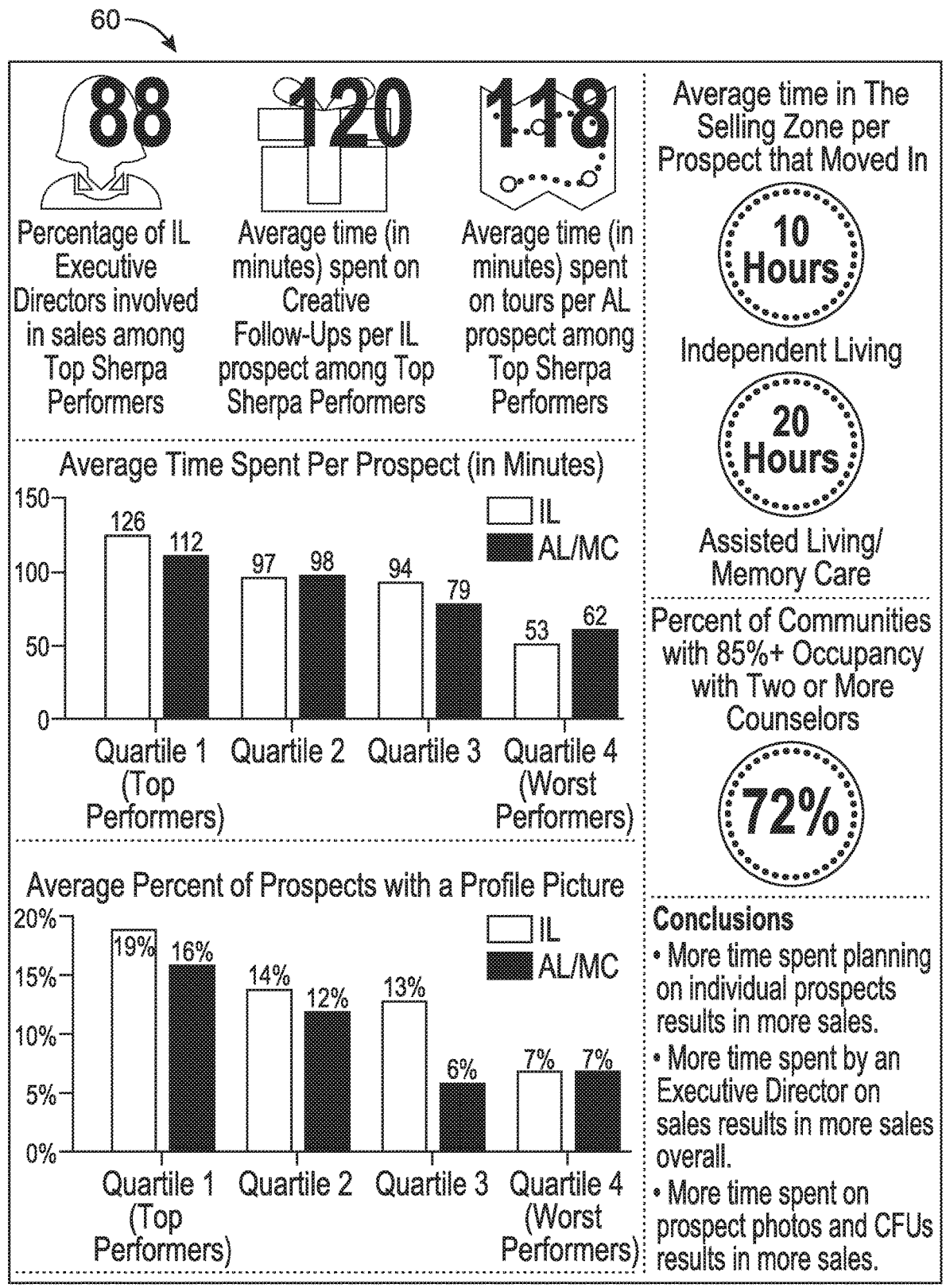
FIG. 10 is a chart illustrating parameters of the research study of FIG. 9.

FIG. 9 is a chart representing a marketing and research study 60 conducted utilizing the data management system 10 and the impact of activities on conversion ration by sales personnel 46 of the data management system 10. FIG. 10 is a graph illustrating parameters of the research study 60 of the data management system 10. The study 60 analyzed encounters between sales counselors 46 and prospects 48. In particular, the scope of the study included: 302,159 sales interactions; 502 sales people, 23,480 leads, 106 communities, and 25 companies across 25 states. The findings of the study 60 included: spending more time on each prospect 48, rather than contacting as many leads as possible, is the most successful way to convert senior living prospect 48s. The study indicated that this finding dispels the customary beliefs that amassing more leads, make more call outs, and conducting more tours results in higher conversions. In the study, the top performers generated 7.5 times the number of call-ins from existing prospects 48 for every call out the performers made.

Figure 11A:
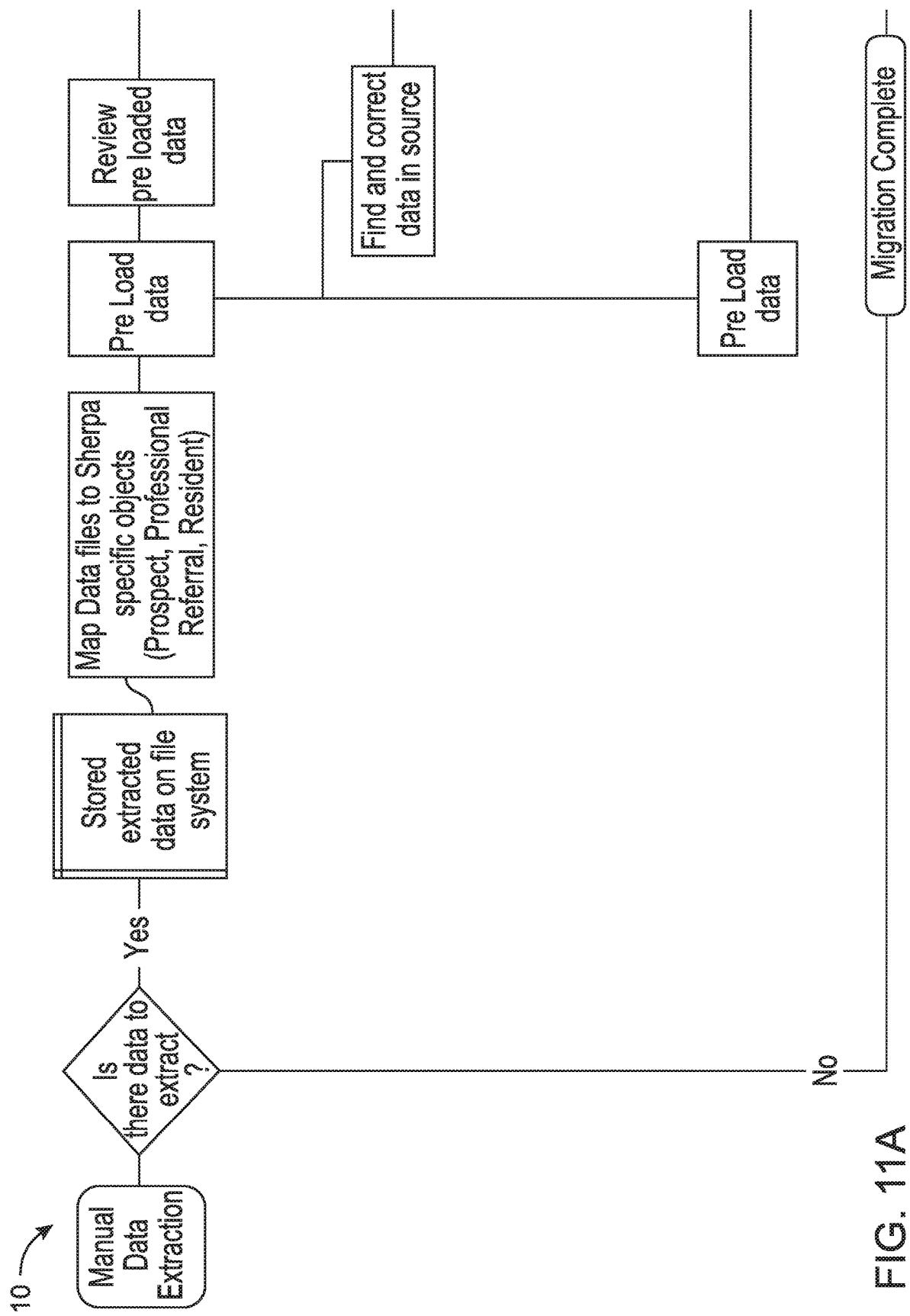
FIGS. 11A-11B depict flowcharts of operation steps used by the data management system which is configured to receive data relating to sale stages of readiness relative to FIGS. 5A-8.
Figure 11B:
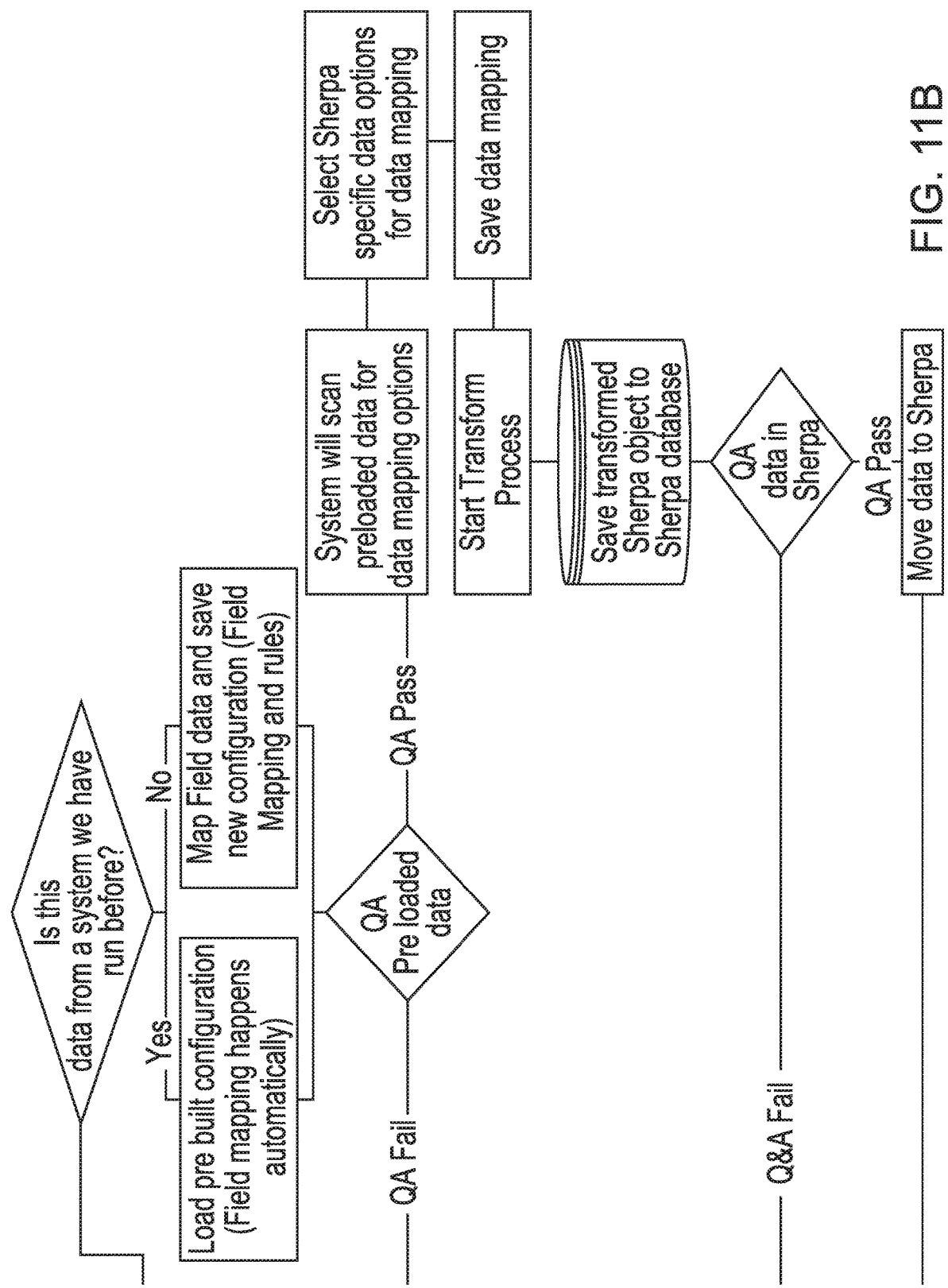

FIGS. 11A-11B depict flowcharts of operation steps used by the data management system 10 which is configured to receive data relating to the four stages of readiness and assess readiness, plan meaningful advances, provide discovery questioning and generate sales pipeline milestones. The data management system 10 is configured to complete or compile conversion ratios for measuring effectiveness for time spent/activity by the sales person 46. The senior housing industry typically recognizes two ratios as lagging sales performance indicators for any specified time frame: i) Number of Initial Tours divided by the number of New Inquiries (Inquiry to Tour Ratio) and ii) Number of Move-Ins divided by the number of Initial Tours (Tour to Move-In or Tour to Close). The processor 14 is configured to calculate these ratios and other ratios which substitute the "Number of Leads or Prospect 48s Worked on" in place of New Inquiries. This distinction changes the focus of the indicator from production based on marketing or new lead generation efforts to one that focuses exclusively and directly on sales performance results.

In the exemplary embodiment, a lead worked includes a lead that has had some activity recorded in a given time period not limited to a direct contact with the lead. For existing leads, the processor 14 is configured to generate conversions which include the following equations:

Leads to Visits=(Tours in a given time period+Home Visits in the same given time period)/Leads Worked in the same given time period  Equation (a);

Leads to Move In=(Tours in a given time period+ Home Visits in the same given time period)/ Move Ins in the same given time period  Equation (b); and Visits to Move Ins=Move Ins within a given time period/(Tours in the same given time period+ Home Visits within the same given time period)  Equation (c);

In the exemplary embodiment, a new lead conversion includes a new lead whose date of inquiry falls within a given time period. For new leads conversion, the processor 14 is configured to generate conversions which include the following equations:

New Leads to Visits=(Tours with new leads in a given time period+Home Visits with new leads in the same given time period)/New Leads from the same given time period  Equation (d);

New Leads to Move In=(Tours with new leads in a given time period+Home Visits with new leads in the same given time period)/Move Ins from the new leads in the same given time period  Equation (e); and Visits to Move Ins=Move Ins from the new leads within a given time period/(Tours with new leads in the same given time period+Home Visits with new leads in the same given time period)  Equation (f).

In other lead management or customer relations management systems, information needed to assess and plan next steps are typically recorded within and as a part of sequential, time stamped sales journal entries. With a conventional approach, the primary way to collect, review and make use of the information is to sort through each individual sales journal note. In the exemplary embodiment, the data management system 10 is configured to separate "what the sales person 46 did" which is captured in a sales journal entry from "what the sales person 46 learned". The data management system 10 is configured to generate a prospect case study format to holistically collect and aggregate information impacting the buying decision based on specific topics or content relative to the stages of readiness.

Within a sales journaling work flow of the data management system 10, the processor 14 is configured to provide the sales person 46 with each entry, provided by the sales person 46 and stored by the memory, to characterize the outcome of each interaction as a "Continuation; Advance; Sale or Lost Lead". This characterization by the processor 14 promotes awareness and determinations regarding the effectiveness of each prospect 48 interaction. The aggregation by the processor 14 of this information, by the prospect 48, a professional referral source, sales counselor, and sales team facilitates providing continuous, actionable sales performance data.

Within the sales journaling work flow of the exemplary embodiment, the processor 14 is configured to generate and send inquiries to the sales person 46 to create a strategic next step as well as a tactic for execution such as, but not limited to, a creative follow up which is unique to the prospect 48. The processor 14 is configured to place the most recent action plan entry on the top of the sales journal entries for each sales person 46.

Moreover, the processor 14 is configured for each prospect 48 and professional contacts to continuously update a "scorecard" that shows: a visual representation of how much the sales person knows; how much time the sales person 46 has invested in the selling zone; what sales activity has occurred; and what sales performance outcomes have been achieved. In the exemplary embodiment, the processor 14 is configured to track sales outcomes for each prospect 48; professional contact; each sales counselor 46 and each sales team 46. The processor 14 rolls up advances and presents the advances to the sales person 46 on an analytics dashboard and in various reports based on at least one of specific time frames, care levels, communities, and regions.

FIGS. 12-17 illustrate exemplary screenshots or tables relating to generating the process for the different stages of the sales method. FIGS. 12A-12B depict exemplary screenshots of a web page showing a team progress for a particular time of the prospect-centered sales process. The exemplary screenshot further illustrates tasks for particular sales personnel and a schedule for face to face visits with prospects 48. FIGS. 13A-13B depict exemplary screenshots of a web page showing a guide for stages of the prospect-centered selling process. FIGS. 14A-14B depict exemplary screenshots of an exemplary web page showing a start stage of the prospect-centered selling process. FIGS. 15A-15E illustrate exemplary web pages showing biography information of a prospect 48. FIGS. 16A-16D illustrate exemplary technical specifications of the data management system 10.

FIG. 17 is an exemplary comparison report of two communities that utilize the prospect-centered selling of the data management system 10. The data management system 10 is configured to compile the prospect data for a plurality of prospects 48 or a plurality of communities. The data management system 10 is configured to conduct data analytics for the compiled prospect data. In particular, the data management system 10 is configured to compare multiple communities that utilize the prospect-centered selling process for ongoing management of sales information. The data management system 10 is configured to compile and compare the distribution of the sales activity types for each individual community. Moreover, the data management system 10 is configured to analyze the move in averages for type of sales activity.

A technical effect of the systems and methods described herein includes at least one of: (a) receiving data, at a processor, associated with the prospect; storing the received prospect data in a memory; (b) analyzing, at the processor, the prospect data; (c) generating, at the processor, a sales plan based at least on the analyzed data by generating at least one guideline; (d) transmitting the at least one guideline to a sales member; (e) receiving, at the processor, feedback data associated with the at least one guideline; and (f) analyzing, at the processor, the received feedback data to determine at least one updating at the processor, the sales plan based at least on the analyzed feedback data.

In the specification and the claims, reference will be made to a number of terms, which shall be defined to have the following meanings. The singular forms "a", "an", and "the" include plural references unless the context clearly dictates otherwise. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Processor is not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not limited to, a scanner. Furthermore, in the exemplary embodiment, additional output channels may include, but not be limited to, an operator interface monitor. The above examples are exemplary only, and thus are not intended to limit in any way the definition and/or meaning of the term processor.

Exemplary embodiments of resource management system are described herein. The methods and systems are not limited to the specific embodiments described herein, but rather, components of systems and/or steps of the methods may be utilized independently and separately from other components and/or steps described herein. For example, the methods may also be used in combination with other manufacturing systems and methods, and are not limited to practice with only the systems and methods as described herein. Rather, the exemplary embodiment may be implemented and utilized in connection with many task, project, and/or sales applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer implemented method for managing sales information associated with a prospect, the method comprising:
 receiving data, at a processor, associated with the prospect;
 storing the received prospect data in a memory;
 analyzing, at the processor, the prospect data;
 generating, at the processor, a sales plan based at least on the analyzed data by generating at least one guideline;
 transmitting the at least one guideline to a sales member;
 receiving, at the processor, feedback data associated with the at least one guideline;
 analyzing, at the processor, the received feedback data to determine at least one analyzed feedback data;
 updating at the processor, the sales plan based at least on the analyzed feedback data;
 determining the real-time conditions associated with the prospect based on the received prospect data;
 automatically selecting a plurality of secondary information associated with the real-time conditions, wherein the secondary information is retrieved from a knowledge base; and
 providing the sales plan and the secondary information in an encounter graphical user interface (GUI) by dynamically populating a visualization space of the GUI based on one or more expressions that are assigned to the visualization space.

2. The computer implemented method of claim 1 further comprising comparing the prospect data with at least one previous prospect data.

3. The computer implemented method of claim 1, further comprising:
receiving an expression from a user along with an associated place holder location in the visualization space;
assigning the expression to a place holder in the visualization space;
processing the sales plan and the secondary information with the expression to determine with a criteria associated with the expression is satisfied; and
populating the place holder in the visualization space depending upon whether the expression criteria is satisfied.

4. The computer implemented method of claim 1, further comprising:
receiving an expression from a user along with an associated location in the visualization space;
processing the sales plan and the secondary information with the expression to determine with a criteria associated with the expression is satisfied; and
dynamically adjusting the encounter GUI depending upon whether the expression criteria is satisfied.

5. The computer implemented method of claim 4 further comprising:
adding a GUI element to the encounter GUI if the expression criteria is satisfied.

6. The computer implemented method of claim 4 further comprising:
removing a GUI element from the encounter GUI if the expression criteria is satisfied.

7. The computer implemented method of claim 4 further comprising:
dynamically adjusting the encounter GUI by adding or removing a GUI element depending upon whether the expression criteria is satisfied, wherein the GUI element is configured to provide guidance information for each selected location.

8. The computer implemented method of claim 1 wherein the at least one guideline comprises presenting acknowledgement of the prospect's autonomy.

9. The computer implemented method of claim 1 wherein the at least one guideline comprises presenting clarifying questions regarding the prospect's current living condition.

10. The computer implemented method of claim 1 wherein the at least one guideline comprises presenting inquiries about the benefit of making a living change.

11. The computer implemented method of claim 1 wherein the at least one guideline comprises providing relevant information about senior housing and committing to opportunities for the prospect to a visit.

12. The computer implemented method of claim 1 wherein generating the sales plan comprises calculating a conversion ration defined by:

$$\text{Leads to Visits} = (\text{Tours in a given time period} + \text{Home Visits in the same given time period})/\text{Leads Worked in the same given time period} \quad \text{Equation (a)}.$$

13. The computer implemented method of claim 1 wherein generating the sales plan comprises calculating a conversion ration defined by:

$$\text{Leads to Move In} = (\text{Tours in a given time period} + \text{Home Visits in the same given time period})/\text{Move Ins in the same given time period} \quad \text{Equation (b)}.$$

14. The computer implemented method of claim 1 wherein generating the sales plan comprises calculating a conversion ration defined by:

$$\text{Visits to Move Ins} = \text{Move Ins within a given time period}/(\text{Tours in the same given time period} + \text{Home Visits within the same given time period}) \quad \text{Equation (c)}.$$

15. The computer implemented method of claim 1 wherein generating the sales plan comprises calculating a conversion ration defined by:

$$\text{New Leads to Visits} = (\text{Tours with new leads in a given time period} + \text{Home Visits with new leads in the same given time period})/\text{New Leads from the same given time period} \quad \text{Equation (d)}.$$

16. The computer implemented method of claim 1 wherein generating the sales plan comprises calculating a conversion ration defined by:

$$\text{New Leads to Move In} = (\text{Tours with new leads in a given time period} + \text{Home Visits with new leads in the same given time period})/\text{Move Ins from the new leads in the same given time period} \quad \text{Equation (e)}.$$

17. The computer implemented method of claim 1 wherein generating the sales plan comprises calculating a conversion ration defined by:

$$\text{Visits to Move Ins} = \text{Move Ins from the new leads within a given time period}/(\text{Tours with new leads in the same given time period} + \text{Home Visits with new leads in the same given time period}) \quad \text{Equation (f)}.$$

18. A computer device for managing for managing sales information associated with a prospect, the computer device comprising:
a memory device configured to store the sales information;
an interface device coupled to the memory device and configured to receive input instructions;
a processor coupled to the memory device and the interface device, the processor programmed to:
receive data, at a processor, associated with the prospect;
store the received prospect data in a memory;
analyze, at the processor, the prospect data;
generate, at the processor, a sales plan based at least on the analyzed data by generating at least one guideline;
transmit the at least one guideline to a sales member;
receive, at the processor, feedback data associated with the at least one guideline;
analyze, at the processor, the received feedback data to determine at least one analyzed feedback data;
update, at the processor, the sales plan based at least on the analyzed feedback data;
determine the real-time conditions associated with the prospect based on the received prospect data;
automatically select a plurality of secondary information associated with the real-time conditions, wherein the secondary information is retrieved from a knowledge base; and
provide the sales plan and the secondary information in an encounter graphical user interface (GUI) by dynamically populating a visualization space of the GUI based on one or more expressions that are assigned to the visualization space.

19. The computer device of claim 18 wherein the at processor is further configured to:
receive an expression from a user along with an associated place holder location in the visualization space;
assign the expression to a place holder in the visualization space;

process the sales plan and the secondary information with the expression to determine with a criteria associated with the expression is satisfied; and populate the place holder in the visualization space depending upon whether the expression criteria is satisfied.

20. One or more non-transitory computer-readable media having computer-executable instructions embodied thereon for managing sales information using a computer device having a memory and a processor, wherein when executed by the processor, the computer-executable instructions cause the processor to:

receive data, at a processor, associated with the prospect;
store the received prospect data in a memory;
analyze, at the processor, the prospect data;
generate, at the processor, a sales plan based at least on the analyzed data by generating at least one guideline;
transmit the at least one guideline to a sales member;
receive, at the processor, feedback data associated with the at least one guideline;
analyze, at the processor, the received feedback data to determine at least one analyzed feedback data;
update, at the processor, the sales plan based at least on the analyzed feedback data;
determine the real-time conditions associated with the prospect based on the received prospect data;
automatically select a plurality of secondary information associated with the real-time conditions, wherein the secondary information is retrieved from a knowledge base; and
provide the sales plan and the secondary information in an encounter graphical user interface (GUI) by dynamically populating a visualization space of the GUI based on one or more expressions that are assigned to the visualization space.

* * * * *